United States Patent
Bando et al.

(10) Patent No.: US 9,745,394 B2
(45) Date of Patent: Aug. 29, 2017

(54) CONJUGATED DIENE POLYMER AND METHOD FOR PRODUCING SAME

(71) Applicants: ZEON CORPORATION, Chiyoda-ku, Tokyo (JP); KYOTO UNIVERSITY, Sakyo-ku, Kyoto (JP)

(72) Inventors: Fumiaki Bando, Tokyo (JP); Shingo Okuno, Tokyo (JP); Shigetaka Hayano, Tokyo (JP); Mitsuo Sawamoto, Kyoto (JP); Makoto Ouchi, Kyoto (JP)

(73) Assignees: ZEON CORPORATION, Tokyo (JP); KYOTO UNIVERSITY, Kyoto (JP)

( * ) Notice: Subject to any disclaimer, the term of this patent is extended or adjusted under 35 U.S.C. 154(b) by 0 days.

(21) Appl. No.: 14/970,183

(22) Filed: Dec. 15, 2015

(65) Prior Publication Data
US 2016/0096910 A1  Apr. 7, 2016

Related U.S. Application Data

(62) Division of application No. 14/344,118, filed as application No. PCT/JP2012/072487 on Sep. 4, 2012, now Pat. No. 9,243,100.

(30) Foreign Application Priority Data

Sep. 12, 2011  (JP) ................. 2011-198209

(51) Int. Cl.

| | |
|---|---|
| C08F 36/04 | (2006.01) |
| C08F 236/04 | (2006.01) |
| C08F 236/06 | (2006.01) |
| C08F 236/08 | (2006.01) |
| C08F 236/10 | (2006.01) |
| C08F 236/16 | (2006.01) |
| C08F 4/80 | (2006.01) |
| C07F 17/02 | (2006.01) |
| C08F 136/08 | (2006.01) |
| C07F 9/50 | (2006.01) |
| C08C 19/12 | (2006.01) |
| C07F 15/00 | (2006.01) |
| C08F 236/12 | (2006.01) |
| C08F 4/72 | (2006.01) |

(52) U.S. Cl.
CPC .......... *C08F 136/08* (2013.01); *C07F 9/5022* (2013.01); *C07F 15/0046* (2013.01); *C07F 17/02* (2013.01); *C08C 19/12* (2013.01); *C08F 4/80* (2013.01); *C08F 36/04* (2013.01); *C08F 236/04* (2013.01); *C08F 236/08* (2013.01); *C08F 236/10* (2013.01); *C08F 236/12* (2013.01); *C08F 236/16* (2013.01); *C08F 4/72* (2013.01)

(58) Field of Classification Search
CPC ...... C08F 36/04; C08F 236/04; C08F 236/06; C08F 236/08; C08F 236/16; C08F 236/10; C08F 4/72; C07F 17/02
See application file for complete search history.

(56) References Cited

U.S. PATENT DOCUMENTS

| 6,653,430 B1 | 11/2003 | Soga et al. |
|---|---|---|
| 2002/0156196 A1 | 10/2002 | Saito et al. |

FOREIGN PATENT DOCUMENTS

| EP | 0 397 081 A2 | 11/1990 |
|---|---|---|
| EP | 1054026 A1 | 11/2000 |
| GB | 1199161 A | 7/1970 |
| GB | 1476500 A | 6/1977 |
| JP | 7-59601 B2 | 6/1995 |
| JP | 07-292038 A | 11/1995 |
| JP | 2000-086719 A | 3/2000 |
| JP | 2002-080523 A | 3/2002 |
| JP | 2002-249505 A | 9/2002 |

(Continued)

OTHER PUBLICATIONS

Baratta et al., "Half-Sandwich Ruthenium(II) Complexes as Catalysts for Stereoselective Carbene-Carbene Coupling Reactions," Organometallics, vol. 18, No. 24, Nov. 1, 1999 (published on the web Nov. 6, 1999), pp. 5091-5096.

(Continued)

*Primary Examiner* — Caixia Lu
(74) *Attorney, Agent, or Firm* — Birch, Stewart, Kolasch & Birch, LLP

(57) ABSTRACT

Conjugated diene polymer comprising at least a conjugated diene monomer unit, the conjugated diene polymer has a number-average molecular weight (Mn) in terms of polystyrene of 1,000 to 1,000,000, a ratio (Mw/Mn) of a weight-average molecular weight (Mw) to the number-average molecular weight (Mn) of lower than 2.0 and the polymer bears a halogen atom at a terminal of the polymer chain. Method for producing the conjugated diene polymer comprises subjecting a monomer containing at least a conjugated diene to living radical polymerization using a polymerization initiator comprising a halogenocyclopentadienyl triorganophosphine $\eta^2$-olefin ruthenium complex represented by formula (6) (and an organic halide.

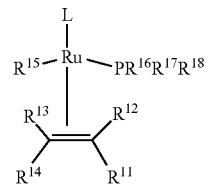

(6)

20 Claims, 5 Drawing Sheets

(56) References Cited

FOREIGN PATENT DOCUMENTS

JP         2003-321509 A     11/2003
JP         2004-203922 A     7/2004

OTHER PUBLICATIONS

Braun et al., "Synthesis, Molecular Structure, and C—C Coupling Reactions of Carbeneruthenium(II) Complexes with $C_5H_5Ru(=CRR')$ and $C_5Me_5Ru(=CRR')$ as Molecular Units," Chem. Eur. J., vol. 9, No. 11, Jun. 3, 2003, pp. 2516-2530.
Extended European Search Report, dated Jun. 9, 2015, for European Application No. 12832404.3.
Hirao et al., "Synthesis of End-Functionalized Polymers by Means of Living Anionic Polymerization. 8. Reactions of Living Anionic Polymers with α,ω-Dihaloalkanes," Macromolecules, vol. 30, No. 12, 1997 (Web Publication Date: Jun. 16, 1997), pp. 3484-3489.
International Search Report for PCT/JP2012/072487 dated Dec. 4, 2012.
Supplementary Partial European Search Report, dated Feb. 16, 2015, for European Application No. 12832404.3.
U.S. Notice of Allowance dated Sep. 16, 2015 for U.S. Appl. No. 14/344,118.
U.S. Office Action dated May 20, 2015 for U.S. Appl. No. 14/344,118.

CONJUGATED DIENE POLYMER AND METHOD FOR PRODUCING SAME

CROSS REFERENCE TO RELATED APPLICATION

This application is a Divisional of co-pending U.S. application Ser. No. 14/344,118 filed on Mar. 11, 2014, which was filed as the National Stage of PCT International Application No. PCT/JP2012/072487 on Sep. 4, 2012, which claims the benefit under 35 U.S.C. §119(a) to Japanese Patent Application No. 2011-198209 filed on Sep. 12, 2011, all of which are hereby expressly incorporated by reference into the present application.

FIELD OF INVENTION

The present invention relates to a conjugated diene polymer and a method for producing the same. More particularly, the present invention relates to a conjugated diene polymer that bears a halogen atom at a terminal of a polymer chain, has a desired molecular weight and a narrow desired molecular weight distribution, and has excellent moldability, and a method for producing the same.

BACKGROUND ART

The conjugated diene polymers such as a styrene/butadiene rubber and a nitrile rubber have a wide range of applications. These conjugated diene polymers have been generally produced by a radical polymerization method using a polymerization initiator such as an azo initiator, an organic peroxide, a persulphate or the like.

However, in radical polymerization of a conjugated diene, it has been difficult to control a molecular weight, a molecular weight distribution, a branch structure, and the like of a conjugated diene polymer to be obtained. Therefore, there have been involved such a problem that the conjugated diene polymer to be obtained is inferior in moldability, controllability during molding, and the like.

In order to widen the application range of a conjugated diene polymer to various materials, a conjugated diene polymer having a desired functional group at a terminal of a polymer chain is desired. However, it has been difficult to obtain directly such a polymer by a radical polymerization method.

A method of obtaining a conjugated diene polymer, subsequently introducing a halogen atom to a terminal of the polymer chain, and then converting the halogen atom into various functional groups can be considered for the introduction of a desired functional group to a terminal of a polymer chain.

For the production of the polymer bearing a halogen atom at a terminal of a polymer chain, there has been known a method of converting the hydroxy group of the copolymer having a hydroxy group at a terminal of a polymer chain into a halogen atom (see, for example, PATENT LITERATURE 1).

This method, however, has a defect that, since the halogen atom adds to the olefin structure moiety of the main chain as well as a terminal of a polymer chain upon replacing the hydroxy group at a terminal of a polymer chain by a halogen atom, inherent characteristics of the conjugated diene polymer are lost.

Therefore, although a halogen atom can be introduced into a terminal of a polymer chain, the resulting polymer is inferior in moldability and controllability during molding, and, hence, there is involved such a problem that the application range as materials is limited.

On the other hand, according to an anion polymerization method applied to the production of styrene/butadiene rubber and the like, a conjugated diene polymer, having a molecular weight, a molecular weight distribution, a branch structure and the like controlled, can be obtained. The conjugated diene polymer thus obtained is excellent in moldability and controllability during molding. In the anion polymerization method, however, the kind of the functional group capable of being introduced to a terminal of a polymer chain is limited, and, hence, it has been difficult to introduce a high reactive halogen atom into a terminal of a polymer chain.

For that reason, after the introduction of, for example, a hydroxy group, a step such as replacement of the hydroxy group by a halogen atom is required, and a hydrogen halide or a thionyl halide must be employed for this replacement. On this replacement, a part of halogen atoms partly add to an olefin structure moiety of a main chain as well as polymer chain terminals, which causes a problem that inherent characteristics of a conjugated diene polymer are lost.

Even in this method, therefore, although a halogen atom can be introduced to a terminal of a polymer chain, the polymer obtained is inferior in moldability and controllability during molding, and, hence, there is involved such a problem that the application range as materials is limited.

In recent years, a polymerization method called living radical polymerization has been studied actively. In living radical polymerization, the activity of a polymerization terminal is not damaged, and molecular weight and molecular weight distribution can be controlled. A polymer bearing a halogen atom at a terminal of a polymer chain can be easily obtained, for example, by polymerizing a radically-polymerizable monomer by living radical polymerization using a polymerization initiator comprising a transition metal complex and an organic halide compound or a sulfonyl halide compound (see, for example, PATENT LITERATURE 2). However, in living radical polymerization, depending on the kind of the monomers to be used, it has been difficult to produce a polymer having a narrow molecular weight distribution while controlling its molecular weight.

Other living radical polymerization methods such as reversible addition-fragmentation chain-transfer polymerization using a thiocarbonyl compound as a chain-transfer agent, nitroxide-mediated polymerization using a radical scavenger such as a nitroxide compound, and the like have been known. In these polymerization methods, use of a halogen-substituted thiocarbonyl compound and a halogen-substituted nitroxide compound permits production of a polymer bearing a halogen atom at a terminal of a polymer chain (see, for example, PATENT LITERATURES 3 and 4). However, since these polymerization methods cause a decrease in the polymerizability of a conjugated diene, it has been very difficult to produce a conjugated diene polymer having a narrow molecular weight distribution while controlling a molecular weight.

As stated above, by these polymerization methods known so far, it has been extremely difficult to obtain a conjugated diene polymer which have a halogen atom at a terminal of a polymer chain and have a desired molecular weight and a desired narrow molecular weight distribution.

LIST OF CITED PATENT LITERATURE

PATENT LITERATURE 1: JP-A61-37804
PATENT LITERATURE 2: JP-A-2005-240048
PATENT LITERATURE 3: JP-A-2002-265508
PATENT LITERATURE 4: JP-A-2000-44610

SUMMARY OF INVENTION

Technical Problem to be Solved

Accordingly, an object of the present invention is to provide a conjugated diene polymer which bears a halogen atom at a terminal of a polymer chain, has a desired molecular weight and a desired narrow molecular weight distribution, and has excellent moldability, and a method for producing the same.

Solution

The present inventors have made extensive investigation to achieve the above-described objects, and have found that a conjugated diene polymer bearing a halogen atom at an end of a polymer chain, and having a number-average molecular weight (Mn) in terms of polystyrene of 1,000 or higher and a ratio (Mw/Mn) of a weight-average molecular weight (Mw) to the number-average molecular weight (Mn) of lower than 2.0, can be obtained by polymerizing a monomer comprising a conjugated diene monomer using a polymerization initiator comprising a specific ruthenium complex and an organic halide, and this conjugated diene polymer has excellent moldability. The present invention has been accomplished on the basis of this finding.

Thus, according the present invention, there is provided a conjugated diene polymer comprising at least a conjugated diene monomer unit, wherein a number-average molecular weight (Mn) in terms of polystyrene is 1,000 or higher and 1,000,000 or lower, a ratio (Mw/Mn) of a weight-average molecular weight (Mw) to the number-average molecular weight (Mn) (hereinafter, sometimes referred to as "polydispersity") is lower than 2.0, and the polymer bears a halogen atom at a terminal of a polymer chain.

The conjugated diene polymer preferably has at least one group selected from among a group represented by general formula (1), a group represented by general formula (2), and a group represented by general formula (3), which are derived from a conjugated diene, a conjugated diene, and a comonomer, respectively, as a polymer chain end group.

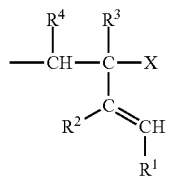

(1)

(In general formula (1), X represents a chlorine atom, a bromine atom or an iodine atom; and $R^1$, $R^2$, $R^3$ and $R^4$ each represent a hydrogen atom, an optionally substituted hydrocarbon group having 1 to 10 carbon atoms, or a halogen atom.)

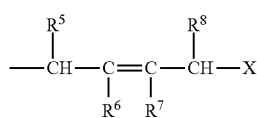

(2)

(In general formula (2), X represents a chlorine atom, a bromine atom, or an iodine atom; and $R^5$, $R^6$, $R^7$ and $R^8$ each represent a hydrogen atom, an optionally substituted hydrocarbon group having 1 to 10 carbon atoms, or a halogen atom.)

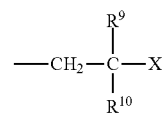

(3)

(In general formula (3), X represents a chlorine atom, a bromine atom or an iodine atom; $R^9$ represents an aryl group, a cyano group, an ester group represented by general formula (4), an amide group represented by general formula (5), or a halogen atom; and $R^{10}$ represents a hydrogen atom or a methyl group.)

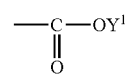

(4)

(In general formula (4), $Y^1$ represents a hydrogen atom or an optionally substituted organic group having 1 to 10 carbon atoms.)

[Chem. 5]

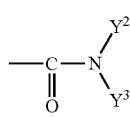

(5)

(In general formula (5), $Y^2$ and $Y^3$ each represent a hydrogen atom or an optionally substituted organic group having 1 to 10 carbon atoms, and $Y^2$ and $Y^3$ may be the same as or different from each other; and the organic group is preferably a hydrocarbon group.)

The conjugated diene polymer of the present invention is preferably one in which 10% or higher of the all polymer chains have a halogen atom at a terminal of a polymer chain.

According to the present invention, there is provided a method for producing the above-described conjugated diene polymer which comprises subjecting a monomer containing at least a conjugated diene to living radical polymerization using a polymerization initiator comprising a halogenocyclopentadienyl triorganophosphine η²-olefin ruthenium complex represented by general formula (6) and an organic halide.

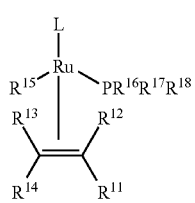

(6)

(In general formula (6), $R^{11}$, $R^{12}$, $R^{13}$ and $R^{14}$ each represent a hydrogen atom, a cyano group, a carbonyl group represented by general formula (7), an ester group represented by general formula (8), an amide group represented by general formula (9), a nitro group, or a halogen atom, provided that at least one of $R^{11}$, $R^{12}$, $R^{13}$ and $R^{14}$ is not a hydrogen atom; $R^{15}$ represents a chlorine atom, a bromine atom or an iodine atom; $R^{16}$, $R^{17}$ and $R^{18}$ each represent an optionally substituted organic group having 1 to 10 carbon atoms, and $R^{16}$, $R^{17}$ and $R^{18}$ may be the same as or different from each other; and L represents an optionally substituted cyclopentadienyl ring.)

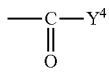

(7)

(In general formula (7), $Y^4$ represents a hydrogen atom or an optionally substituted hydrocarbon group having 1 to 10 carbon atoms.)

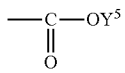

(8)

(In general formula (8), $Y^5$ represents a hydrogen atom or an optionally substituted organic group having 1 to 10 carbon atoms.)

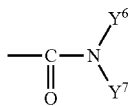

(9)

(In general formula (9), $Y^6$ and $Y^7$ each represent a hydrogen atom or an optionally substituted hydrocarbon group having 1 to 10 carbon atoms.)

In the method for producing the conjugated diene polymer of the present invention, the ligand represented by general formula (10) in the complex of general formula (6) may be an electron-withdrawing olefin copolymerizable with a conjugated diene monomer.

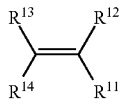

(10)

(In general formula (10), $R^{11}$, $R^{12}$, $R^{13}$ and $R^{14}$ are the same as those of general formula (6).)

In the method for producing the conjugated diene polymer of the present invention, the polymerization can be carried out by adding a monomer, containing at least a conjugated diene monomer, and an organic halide to a halogenocyclopentadienyl triorganophosphine $\eta^2$-olefin ruthenium complex represented by general formula (6) in a polymerization solvent.

In the method for producing the conjugated diene polymer of the present invention, the polymerization can be carried out by causing a halogenocyclopentadienyl bis(triorganophosphine) ruthenium represented by general formula (11) to react with an electron-withdrawing olefin represented by general formula (10) in a polymerization solvent to form a halogenocyclopentadienyl triorganophosphine $\eta^2$-olefin ruthenium complex represented by general formula (6) in the reaction system and adding a monomer, containing at least a conjugated diene monomer, and an organic halide thereto.

[Chem. 11]

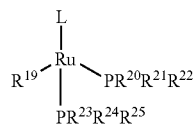

(11)

(In general formula (11), L is the same as L of general formula (6); $R^{19}$ is the same as $R^{15}$ of general formula (6); $R^{20}$ to $R^{25}$ each represent an optionally substituted organic group having 1 to 10 carbon atoms and may be the same as or different from each other, and the organic group is preferably a hydrocarbon group, and $R^{16}$ to $R^{18}$ of general formula (6) correspond to $R^{20}$ to $R^{22}$, or $R^{23}$ to $R^{25}$, respectively.)

In the method for producing the conjugated diene polymer of the present invention, the polymerization can be carried out by causing a halogenocyclopentadienyl ruthenium tetramer represented by general formula (12), a phosphine compound represented by $PR^{16}R^{17}R^{18}$ ($R^{16}$, $R^{17}$ and $R^{18}$ are the same as those of general formula (6)), and an electron-withdrawing olefin represented by general formula (10) to react in a polymerization solvent to form a halogenocyclopentadienyl triorganophosphine $\eta^2$-olefin ruthenium complex represented by general formula (6) in the reaction system, and adding a monomer, containing at least a conjugated diene monomer, and an organic halide thereto.

$$[LRu(\mu_3\text{-}X)]_4 \quad (12)$$

(In general formula (12), L is the same as that of general formula (6); and X represents a chlorine atom, a bromine atom or an iodine atom.)

In the method for producing the conjugated diene polymer of the present invention, a monomer containing a conjugated diene can be subjected to living radical polymerization using a polymerization initiator comprising a halogenocyclopentadienyl triorganophosphine $\eta^2$-olefin ruthenium complex represented by general formula (6) and an organic halide in combination with an organic amine or a metal alkoxide as an activator.

In the method for producing the conjugated diene polymer of the present invention, a monomer containing a conjugated diene monomer can be subjected to living radical polymerization using a polymerization initiator comprising a halogenocyclopentadienyl triorganophosphine $\eta^2$-olefin ruthenium complex represented by general formula (6) and an organic halide, and an organic amine or a metal alkoxide as an activator in combination with a radical generator further.

In the method for producing the conjugated diene polymer of the present invention, a phosphine as a stabilizer can be added to the polymerization reaction system.

In the method for producing the conjugated diene polymer of the present invention, a cyclic ester or a cyclic carbonate can be used as a polymerization solvent.

According to the present invention, a halogenocyclopentadienyl triorganophosphine $\eta^2$-olefin ruthenium complex represented by formula (6), in which at least two of $R^{11}$, $R^{12}$, $R^{13}$ and $R^{14}$ are not a hydrogen atom, is provided.

Advantageous Effects of Invention

According to the present invention, there are provided a conjugated diene polymer which bears a halogen atom at a terminal of a polymer chain, permits easy introduction of a desired functional group to a terminal of a polymer chain by using the halogen atom, and has excellent moldability, and a method for producing the same and a novel ruthenium complex.

MODES FOR CARRYING OUT THE INVENTION

Figure 1:
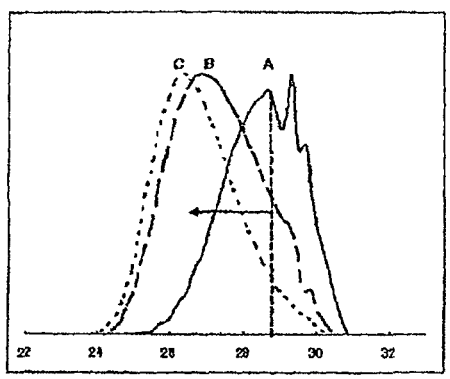
FIG. 1 is a chart of a gel permeation chromatography (GPC) showing a change, with the passage of time, of the molecular weight of the polymer in terms of polystyrene in the reaction system during the polymer production in Example 1.

The conjugated diene polymer of the present invention is a conjugated diene polymer comprising at least a conjugated diene monomer unit, wherein the conjugated diene polymer has a number-average molecular weight (Mn) in terms of polystyrene of 1,000 or higher and 1,000,000 or lower, a ratio (Mw/Mn) (polydispersity) of the weight-average molecular weight (Mw) to a number-average molecular weight (Mn) of lower than 2.0 and the polymer bears a halogen atom at a terminal of the polymer chain.

The conjugated diene to be used as a monomer for the conjugated diene polymer of the present invention is not particularly limited and includes, for example, 1,3-butadiene, isoprene (2-methyl-1,3-butadiene), 1,3-pentadiene, 2-ethyl-1,3-butadiene, 2,3-dimethyl-1,3-butadiene, 2-methyl-1,3,-pentadiene, 4-methyl-1,3-pentadiene, 1,3-hexadiene, 2,4-hexadiene, 3,4-dimethyl-1,3-hexadiene, 4,5-dimethyl-1,3-octadiene, 3-butyl-1,3-octadiene, chloroprene, and the like.

These conjugated dienes may be used either singly or in combination of two or more thereof.

Among the conjugated dienes, 1,3-butadiene, isoprene, or 1,3-pentadiene is preferably used.

The conjugated diene polymer of the present invention may be either one comprising only a conjugated diene monomer unit as a monomer unit or one comprising a conjugated diene monomer unit and other monomer units. In the conjugated diene polymer of the present invention, the content of the conjugated diene monomer units to all monomer units is not particularly limited. However, the content thereof is generally 1% by weight or higher, preferably 10% by weight or higher, more preferably 20% by weight or higher.

The monomer, which can be used, together with a conjugated diene monomer as a monomer for the conjugated diene polymer of the present invention, is not particularly limited. However, a radically polymerizable monomer is preferred.

Specific examples thereof include aromatic vinyl monomers such as styrene, α-methylstyrene, p-methylstyrene, p-chlorostyrene, vinyltoluene and the like; ethylenically unsaturated nitrile monomers such as acrylonitrile, methacrylonitrile and the like; (meth)acrylic esters such as 2methoxyethyl (meth)acrylate, 2phenoxyethyl (meth)acrylate, 3methoxybutyl (meth)acrylate, 2hydroxyethyl (meth)acrylate, 2hydroxypropyl (meth)acrylate, methoxy diethylene glycol (meth)acrylate, ethoxy diethylene glycol (meth)acrylate, phenoxy diethylene glycol (meth)acrylate, methoxy triethylene glycol (meth)acrylate, ethoxy triethylene glycol (meth)acrylate, methoxy tetraethylene glycol (meth)acrylate, ethoxy tetraethylene glycol (meth)acrylate, glycidyl (meth)acrylate, phenyl (meth)acrylate, chlorophenyl (meth)acrylate, bromophenyl (meth)acrylate, benzyl (meth)acrylate, chlorobenzyl (meth)acrylate, bromobenzyl (meth)acrylate, chloroethyl (meth)acrylate, bromoethyl (meth)acrylate and the like; (meth)acrylic acids such as acrylic acid, methacrylic acid and the like; and acrylamides such as acrylamide, N,N-dimethylacrylamide, N,N-diisopropylacrylamide and the like. Among these, aromatic vinyl monomers, (meth)acrylic esters, (meth)acrylic acids and ethylenically unsaturated nitriles are preferred, and among them further, (meth)acrylic acid esters and ethylenically unsaturated nitriles are particularly preferred.

In the present invention, "(meth)acrylic acids" refers to acrylic acid and/or methacrylic acid.

The microstructure of the conjugated diene monomer unit in the conjugated diene polymer of the present invention is not particularly limited. However, the proportion of the 1,4-bond conjugated diene monomer units in all conjugated diene monomer units is preferably 50% by mole or higher, more preferably 60% by mole or higher, even more preferably 70% by mole or higher.

The number-average molecular weight (Mn) in terms of polystyrene of the conjugated diene polymer of the present invention is required to be 1,000 or more and 1,000,000 or less, and it is preferably 1,000 to 500,000, more preferably 1,000 to 300,000.

The number-average molecular weight (Mn) in terms of polystyrene of 1,000 or higher ensures moldability as a polymer material and mechanical strength after having been processed. On the other hand, when the number-average molecular weight (Mn) in terms of polystyrene is lower than 1,000, fluidity increases excessively and, hence, the polymer becomes difficult to be processed as a polymer material. Even if cross-linked, the polymer has low strength, and is likely not to exhibit rubber elasticity.

On the other hand, when the number-average molecular weight (Mn) in terms of polystyrene exceeds 1,000,000, the processability is deteriorated greatly and results in difficulty in processing into rubber materials.

The ratio (Mw/Mn) (polydispersity) of the weight-average molecular weight (Mw) to the number-average molecular weight (Mn) in terms of polystyrene of the conjugated diene polymer of the present invention is required to be lower than 2.0. This polydispersity is preferably 1.8 or lower, more preferably 1.6 or lower, even more preferably 1.5 or lower. The polydispersity of not higher than the above-described value ensures moldability as a polymer material and the mechanical strength after having been processed. On the other hand, when the ratio is 2 or higher, processability as a polymer material and mechanical strength after having been processed become likely to be insufficient.

In the present invention, the weight-average molecular weight (Mw), the number-average molecular weight (Mn) and polydispersity (Mw/Mn) of the conjugated diene polymer, are principally determined in terms of polystyrene by gel permeation chromatography (GPC) using tetrahydrofuran (THF) as a solvent (mobile phase) and a polystyrene gel column as a column.

The conjugated diene polymer of the present invention bears a halogen atom at a terminal of a polymer chain. More specifically, it bears a halogen atom at a growth end of a polymer chain. Since a halogen atom at a terminal of a polymer chain is easily converted into other functional groups, a desired functional group can be introduced to a polymer chain depending on the properties required. The kind of a halogen atom is not particularly limited, but is preferably a chlorine atom, a bromine atom or an iodine atom, more preferred a chlorine atom or a bromine atom.

The conjugated diene polymer of the present invention may have a plurality of polymer chain growth terminals, and the conjugated diene polymer may be also one bearing a halogen atom at the respective terminals of a polymer chain, that is, one having a plurality of halogen atoms. Such a conjugated diene polymer can be obtained by, for example, using a polyfunctional initiator bearing a plurality of halogen atoms, in the production method of the conjugated diene polymer of the present invention which will be described later.

In the conjugated diene polymer of the present invention, all polymers constituting the conjugated diene polymer may have a halogen atom at a terminal of the polymer chain or only a part of the polymers may have a halogen atom at a terminal of the polymer chain.

The proportion of the polymer chains bearing a halogen atom at a terminal thereof (proportion relative to the total number of polymer chains) among all polymer chains of all polymers constituting the conjugated diene polymer of the present invention, is not particularly limited. However, the proportion is preferably 50% or higher, more preferably 60% or higher, even more preferably 70% or higher, most preferably 80% or higher.

In the conjugated diene polymer of the present invention, a terminal structure of a polymer chain bearing a halogen atom at a terminal thereof is not particularly limited. However, the terminal structure is preferably a group selected from among a group represented by general formula (1), a group represented by general formula (2), and a group represented by general formula (3).

The groups represented by general formulae (1) and (2) are derived from a conjugated diene monomer and the group represented by general formula (3) is derived from comonomer of conjugated diene.

(In general formula (1), X represents a chlorine atom, a bromine atom or an iodine atom; and $R^1$, $R^2$, $R^3$ and $R^4$ each represent a hydrogen atom, an optionally substituted hydrocarbon group having 1 to 10 carbon atoms, or a halogen atom.)

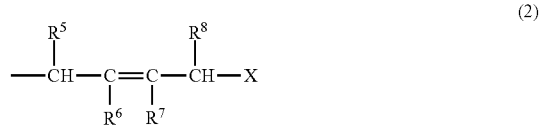

(In general formula (2), X represents a chlorine atom, a bromine atom or an iodine atom. $R^5$, $R^6$, $R^7$ and $R^8$ each represent a hydrogen atom, an optionally substituted hydrocarbon group having 1 to 10 carbon atoms, or a halogen atom.)

(In general formula (3), X represents a chlorine atom, a bromine atom or an iodine atom; $R^9$ represents an aryl group, a cyano group, an ester group represented by general formula (4), an amide group represented by general formula (5), or a halogen atom; and $R^{10}$ represents a hydrogen atom or a methyl group.)

(In general formula (4), $Y^1$ represents a hydrogen atom or an optionally substituted organic group having 1 to 10 carbon atoms.)

(In general formula (5), $Y^2$ and $Y^3$ each represent a hydrogen atom or an optionally substituted organic group having 1 to 10 carbon atoms, and $Y^2$ and $Y^3$ may be the same as or different from each other; and the organic group is preferably a hydrocarbon group.)

The method for producing the conjugated diene polymer of the present invention is not limited so long as the desired polymer is obtained. However, the desired polymer can be easily obtained by employing the method for producing the conjugated diene polymer of the present invention which will be described later.

That is, the method for producing the conjugated diene polymer of the present invention for the production of the conjugated diene polymer of the present invention is characterized in that it comprises subjecting a monomer containing at least a conjugated diene to living radical polymerization using a polymerization initiator comprising a halogenocyclopentadienyl triorganophosphine $\eta^2$-olefin ruthenium complex represented by general formula (6) and an organic halide.

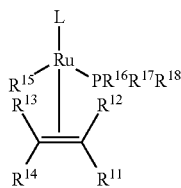
(6)

(In general formula (6), $R^{11}$, $R^{12}$, $R^{13}$ and $R^{14}$ each represent a hydrogen atom, a cyano group, a carbonyl group represented by general formula (7), an ester group represented by general formula (8), an amide group represented by general formula (9), a nitro group, or a halogen atom, provided that at least one of $R^{11}$, $R^{12}$, $R^{13}$ and $R^{14}$ is not a hydrogen atom; $R^{15}$ represents a chlorine atom, a bromine atom, or an iodine atom. $R^{16}$, $R^{17}$ and $R^{18}$ each represent an optionally substituted organic group having 1 to 10 carbon atoms, and $R^{16}$, $R^{17}$ and $R^{18}$ may be the same as or different from each other; and L represents an optionally substituted cyclopentadienyl ring.)

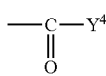
(7)

(In general formula (7), $Y^4$ represents a hydrogen atom or an optionally substituted hydrocarbon group having 1 to 10 carbon atoms.)

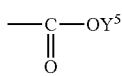
(8)

(In general formula (8), $Y^5$ represents a hydrogen atom or an optionally substituted organic group having 1 to 10 carbon atoms.)

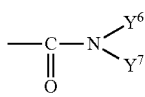
(9)

(In general formula (9), $Y^6$ and $Y^7$ each represent a hydrogen atom or an optionally substituted hydrocarbon group having 1 to 10 carbon atoms.)

In the method for producing the conjugated diene polymer of the present invention, the production of the conjugated diene polymer is facilitated by using a living radical polymerization initiator comprising a halogenocyclopentadienyl triorganophosphine $\eta^2$-olefin ruthenium complex represented by general formula (6), as a transition metal complex, in which an olefin having an electron-withdrawing substituent (electron-withdrawing olefin) is coordinated in combination with an organic halide.

Although the reason is not necessarily clear, it is presumed that the ruthenium complex represented by general formula (6), in which a specific electron-withdrawing olefin is coordinated, has a moderate electron density thereby to hinder a side reaction of the ruthenium complex with an allyl halide structure, as the polymer growth terminal derived from the conjugated diene monomer, and that thus living radical polymerization of a monomer containing a conjugated diene is achieved.

In the halogenocyclopentadienyl triorganophosphine $\eta^2$-olefin ruthenium complex represented by general formula (6), the phosphine compound for the introduction of the ligand $PR^{16}R^{17}R^{18}$ is not particularly limited. However, the groups represented by $R^{16}$, $R^{17}$ and $R^{18}$ are preferably an optionally substituted alkyl group having 1 to 10 carbon atoms, an optionally substituted aryl group having 1 to 10 carbon atoms, an alkoxy group having 1 to 10 carbon atoms or an aryloxy group having 1 to 10 carbon atoms. Examples of the phosphine compounds represented by $PR^{16}R^{17}R^{18}$ include a trialkylphosphine such as triethylphosphine, tributylphosphine and the like; a triarylphosphine such as triphenylphosphine, trinaphthylphosphine, tri(m-tolyl)phosphine, tri(4-methoxyphenyl)phosphine, tri(p-trifluoromethylphenyl)phosphine and the like; a trialkylphosphite such as tributylphosphite and the like; a triarylphosphite such as triphenylphosphite and the like; a bisphosphinoalkane such as 1,2-bis(diphenylphosphino)ethane and the like; a phosphaalkene; and the like. Among these, a triarylphosphine is preferably used.

In general formula (6), the ligand represented by L is not particularly limited so long as it is a cyclopentadienyl ring or a cyclopentadienyl ring having a substituent.

Examples of the substituent include an alkyl group, a cycloalkyl group and an aryl group. The number of the substituents is also not limited. The number of carbon atoms of the substituents is not particularly limited, but is generally 1 to 12.

The substituents on the cyclopentadienyl ring may be further substituted with a phenyl group, an amino group, an alkoxy group or the like.

Examples of the alkyl substituent on the cyclopentadienyl ring include a methyl group, an ethyl group, a propyl group, a butyl group, a hexyl group and the like.

Examples of the cycloalkyl substituent include a cyclopentyl group, a cyclohexyl group and the like.

Examples of the aryl substituent include a phenyl group and the like.

The substituents on the cyclopentadienyl ring may be bonded to each other to form a ring. Specific examples of such substituents include an indenyl group, a 4,5,6,7-tetrahydroindenyl group, a fluorenyl group and the like.

Specific examples of the alkyl-substituted cyclopentadienyl ring include a methylcyclopentadienyl ring, a 1,2-dimethylcyclopentadienyl ring, a 1,3-dimethylcyclopentadienyl ring, a 1,2,3-trimethylcyclopentadienyl ring, a 1,2,4- trimethylcyclopentadienyl ring, 1,2,3,4-tetramethylcyclopentadienyl ring, a pentamethylcyclopentadienyl ring, an ethylcyclopentadienyl ring, a 1-methyl-2-ethylcyclopentadienyl ring, a 1-methyl-3-ethylcyclopentadienyl ring, a propylcyclopentadienyl ring, a 1-methyl-2-propylcyclopentadienyl ring, 1-methyl-3-propylcyclopentadienyl ring, a butyl cyclopentadienyl ring, a 1-methyl-2-butylcyclopentadienyl ring, a 1-methyl-3-butylcyclopentadienyl ring, a hexylcyclopentadienyl ring and the like.

As the ligand represented by L, an alkylcyclopentadienyl ring is more preferably used, and among them, further, a pentamethylcyclopentadienyl ring is especially preferably used.

The halogenocyclopentadienyl triorganophosphine $\eta^2$-olefin ruthenium complex represented by general formula (6) can be obtained by mixing a halogenocyclopentadienyl bis(triorganophosphine) ruthenium complex represented by general formula (11) with an electron-withdrawing olefin and causing them to react.

The electron-withdrawing olefin is represented by general formula (10).

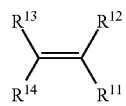

(10)

(In general formula (10), $R^{11}$, $R^{12}$, $R^{13}$ and $R^{14}$ each represent a hydrogen atom, a cyano group, a carbonyl group represented by general formula (7), an ester group represented by general formula (8), an amide group represented by general formula (9), a nitro group, or a halogen atom, provided that at least one of $R^{11}$, $R^{12}$, $R^{13}$ and $R^{14}$ is not a hydrogen atom; and $R^{11}$, $R^{12}$, $R^{13}$ and $R^{14}$ may be bonded to each other to form a ring.)

The electron-withdrawing olefin is preferably an olefin which has a substituent having a stronger electron-withdrawing property, and it is also preferred to have a plurality of electron-withdrawing substituents.

Specific examples of the electron-withdrawing olefin represented by general formula (10) include acrylonitrile, methacrylonitrile, fumaronitrile, vinylidene cyanide, tetracyanoethylene, 2-chloroacrylonitrile, acrolein, methyl vinyl ketone, ethyl vinyl ketone, butyl vinyl ketone, 2methoxyethyl (meth)acrylate, 2phenoxyethyl (meth)acrylate, 3methoxybutyl (meth)acrylate, 2hydroxyethyl (meth)acrylate, 2hydroxypropyl (meth)acrylate, methoxydiethylene glycol (meth)acrylate, ethoxydiethylene glycol (meth)acrylate, phenoxydiethylene glycol (meth)acrylate, methoxytriethylene glycol (meth)acrylate, ethoxytriethylene glycol (meth)acrylate, methoxytetraethylene glycol (meth)acrylate, ethoxytetraethylene glycol (meth)acrylate, glycidyl (meth) acrylate, phenyl (meth)acrylate, chlorophenyl (meth)acrylate, bromophenyl (meth)acrylate, benzyl (meth)acrylate, chlorobenzyl (meth)acrylate, bromobenzyl (meth)acrylate, chloroethyl (meth)acrylate, bromoethyl (meth)acrylate, acrylic acid, methacrylic acid, acrylamide, N,N-dimethylacrylamide, N,N-diisopropylacrylamide, methacrylamide, vinylsulfonic acid, vinyl fluoride, vinyl chloride, vinyl bromide, vinylidene fluoride, tetrafluoroethylene, hexafluoropropylene, maleic anhydride, maleimide, phenylmaleimide, and the like.

The method of mixing a halogenocyclopentadienyl bis(triorganophosphine) ruthenium complex represented by general formula (11) with an electron-withdrawing olefin is not particularly limited, but a method of mixing a halogenocyclopentadienyl bis(triorganophosphine) ruthenium complex represented by general formula (11), which has been dissolved or dispersed in an organic solvent, with an electron-withdrawing olefin alone or an electron-withdrawing olefin that has been dissolved or dispersed in an organic solvent, is preferred.

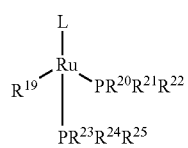

(11)

(In general formula (11), L is the same as L of general formula (6). $R^{19}$ is the same as $R^{19}$ of general formula (6); $R^{20}$ to $R^{25}$ each represent an optionally substituted organic group having 1 to 10 carbon atoms and may be the same as or different from each other; the organic group is preferably a hydrocarbon atom; and $R^{16}$ to $R^{18}$ of general formula (6) correspond to $R^{20}$ to $R^{22}$, or $R^{23}$ to $R^{25}$.)

The organic solvent to be used for the synthesis of the halogenocyclopentadienyl triorganophosphine $\eta^2$-olefin ruthenium complex represented by general formula (6) is not particularly limited so long as it dissolves or disperses the halogenocyclopentadienyl bis(triorganophosphine) ruthenium complex represented by general formula (11) and the electron-withdrawing olefin represented by general formula (10) and does not inhibit the reaction. However, industrial general-purpose solvents are preferred.

Specific examples of such an organic solvent include, for example, an aromatic hydrocarbon solvent such as benzene, toluene, xylene and the like; a halogen-containing aliphatic hydrocarbon solvent such as dichloromethane, chloroform, 1,2-dichloroethane and the like; a halogenated aromatic hydrocarbon solvent such as chlorobenzene, dichlorobenzene and the like; a nitrogen-containing hydrocarbon solvent such as nitromethane, nitrobenzene, acetonitrile and the like; an ether solvent such as diethyl ether, tetrahydrofuran and the like; an aromatic ether solvent such as anisole, phenetole and the like; an aromatic amine solvent such as pyridine, lutidine and the like; an alicyclic hydrocarbon solvent such as cyclohexane, methyl cyclohexane, decahydronaphthalene, bicycloheptane, tricyclodecane, cyclooctane and the like; and the like.

Among these solvents, aromatic hydrocarbon solvents and ether solvents are preferably used. These solvents are excellent in solubility for the halogenocyclopentadienyl bis(triorganophosphine) ruthenium complex represented by general formula (11) and an electron-withdrawing olefin, and hardly exert influences on the subsequent reactions.

The concentrations of the halogenocyclopentadienyl bis(triorganophosphine) ruthenium complex represented by general formula (11) and the electron-withdrawing olefin can be each selected at will.

The halogenocyclopentadienyl bis(triorganophosphine) ruthenium complex and the electron-withdrawing olefin are mixed in an inert gas atmosphere.

The order of mixing the halogenocyclopentadienyl bis(triorganophosphine) ruthenium complex and the electron-withdrawing olefin is not particularly limited. An electron-withdrawing olefin or a solution containing the electron-withdrawing olefin may be added to a solution containing a halogenocyclopentadienyl bis(triorganophosphine) ruthenium complex represented by general formula (11), or vice versa. Or, both solutions may be added into another container at the same time and mixed therein.

The molar ratio of the electron-withdrawing olefin to the halogenocyclopentadienyl bis(triorganophosphine) ruthenium complex represented by general formula (11) (electron-withdrawing olefin/halogenocyclopentadienyl bis(triorganophosphine) ruthenium complex) is preferably 1 to 10,000, more preferably 1 to 1,000, especially preferably 1 to 5. When the molar ratio of the electron-withdrawing olefin to the halogenocyclopentadienyl bis(triorganophosphine) ruthenium complex represented by general formula (11) is less than 1, the halogenocyclopentadienyl bis(triorganophosphine) ruthenium complex remains partly unreacted, thereby exerting unfavorable influences on the polymerization.

The reaction temperature is not particularly limited, but is preferably within the range of from −100° C. to +100° C. Too low a temperature unfavorably results in too slow progress of the reaction, whereas too high a temperature unfavorably causes a side reaction and decomposition of products. The reaction temperature range is more preferably from −80° C. to +80° C. and even more preferably from −70° C. to +70° C. It is also preferred that the mixing is carried out at a low temperature of 0° C. or lower and then the temperature is gradually elevated to room temperature to cause the reaction proceed. The reaction time is not particularly limited as long as it is within the range of from 1 minute to 1 week.

The halogenocyclopentadienyl triorganophosphine $\eta^2$-olefin ruthenium complex represented by general formula (6), which is a reaction product of the halogenocyclopentadienyl bis(triorganophosphine) ruthenium complex represented by general formula (11) and the electron-withdrawing olefin represented by general formula (10), may be recovered by adding the reaction liquid to an organic solvent which does not dissolve the reaction product, for example, a saturated hydrocarbon such as pentane, thereby to precipitate the product or by distilling away the solvent used in the reaction.

Alternatively, the reaction liquid may be used as it is for the following polymerization step. In the case where the reaction liquid is used as it is in the following polymerization step, the electron-withdrawing olefin is preferably a monomer to be used for the polymerization.

Alternatively, the halogenocyclopentadienyl bis(triorganophosphine) ruthenium complex represented by general formula (11) can be synthesized from a halogenocyclopentadienyl ruthenium tetramer represented by general formula (12) and a phosphine compound.

The halogenocyclopentadienyl bis(triorganophosphine) ruthenium complex represented by general formula (11) can be prepared by adding the phosphine compound to the halogenocyclopentadienyl ruthenium tetramer followed by stirring at 80° C. for 1 hour or more. By adding the electron-withdrawing olefin represented by general formula (10) thereto, the halogenocyclopentadienyl triorganophosphine $\eta^2$-olefin ruthenium complex represented by general formula (6) can be obtained. The reaction liquid thus obtained may be used as it is in the polymerization reaction of the conjugated diene monomers.

Specific examples of the halogenocyclopentadienyl triorganophosphine $\eta^2$-olefin ruthenium complex represented by general formula (6) thus obtained include chloropentamethylcyclopentadienyl triphenylphosphine $\eta^2$-acrylonitrile ruthenium, chloro-1,3-dimethylcyclopentadienyl triphenylphosphine $\eta^2$-acrylonitrile ruthenium, chloro-1,2,3,4-tetramethylcyclopentadienyl triphenylphosphine $\eta^2$-acrylonitrile ruthenium, chloropentamethylcyclopentadienyl tributylphosphine $\eta^2$-acrylonitrile ruthenium, chloropentamethylcyclopentadienyl tri(4-methoxyphenyl)phosphine $\eta^2$-acrylonitrile ruthenium, chloropentamethylcyclopentadienyl tri(m-tolyl)phosphine $\eta^2$-acrylonitrile ruthenium, chloropentamethylcyclopentadienyl tri(p-trifluoromethylphenyl)phosphine $\eta^2$-acrylonitrile ruthenium, chloropentamethylcyclopentadienyl 1,2-bis(diphenylphosphino)ethane $\eta^2$-acrylonitrile ruthenium, bromopentamethylcyclopentadienyl triphenylphosphine $\eta^2$-acrylonitrile ruthenium, chloropentamethylcyclopentadienyl triphenylphosphine $\eta^2$-fumaronitrile ruthenium, bromopentamethylcyclopentadienyl triphenylphosphine $\eta^2$-fumaronitrile ruthenium, chloropentamethylcyclopentadienyl triphenylphosphine $\eta^2$-2-chloroacrylonitrile ruthenium, chloropentamethylcyclopentadienyl triphenylphosphine $\eta^2$-acrolein ruthenium, chloropentamethylcyclopentadienyl triphenylphosphine $\eta^2$methyl vinyl ketone ruthenium, chloropentamethylcyclopentadienyl triphenylphosphine $\eta^2$-2-methoxyethyl acrylate ruthenium, chloropentamethylcyclopentadienyl triphenylphosphine $\eta^2$-2-hydroxyethyl acrylate ruthenium, chloropentamethylcyclopentadienyl triphenylphosphine $\eta^2$-glycidyl acrylate ruthenium, chloropentamethylcyclopentadienyl triphenylphosphine $\eta^2$-chloroethyl acrylate ruthenium, chloropentamethylcyclopentadienyl triphenylphosphine $\eta^2$-acrylamide ruthenium, chloropentamethylcyclopentadienyl triphenylphosphine $\eta^2$-N,N-diisopropylacrylamide ruthenium, chloropentamethylcyclopentadienyl triphenylphosphine $\eta^2$-vinylsulfonate ruthenium, chloropentamethylcyclopentadienyl triphenylphosphine $\eta^2$-vinyl fluoride ruthenium, chloropentamethylcyclopentadienyl triphenylphosphine $\eta^2$-vinylidene fluoride ruthenium, chloropentamethylcyclopentadienyl triphenylphosphine $\eta^2$-tetrafluoroethylene ruthenium, chloropentamethylcyclopentadienyl triphenylphosphine $\eta^2$-maleic anhydride ruthenium, chloropentamethylcyclopentadienyl triphenylphosphine $\eta^2$-phenylmaleimide ruthenium, and the like.

Among these, a complex in which a cyano group-containing olefin is $\eta^2$-coordinated and a complex in which an olefin bearing two electron-withdrawing groups is $\eta^2$-coordinated are particularly preferred.

The organic halide to be used as an ingredient of the polymerization initiator used in the method for producing the conjugated diene polymer of the present invention is not particularly limited so long as it is a compound having at least one halogen atom which functions as polymerization starting point. Specific examples of the organic halide include a halogenated aromatic compound, a halogen-substituted carboxylic acid ester, a halogen-substituted ketone, a halogenated allyl compound, a halogen-substituted nitrile compound, an arylsulfonic halide, an alkanesulfonic halide, and the like.

Specific examples of the organic halogen compound having one halogen atom include a halogenated aromatic compound such as phenylmethyl halides, 1-phenylethyl halides and the like; a halogen-substituted carboxylic acid ester such as 1-phenylisopropyl halides, methyl 2-halopropionates, ethyl 2-halopropionates, methyl 2-haloisobutyrates, ethyl 2-haloisobutyrates, methyl α-halophenylacetates, ethyl α-halophenylacetates and the like; a halogen-substituted ketone such as α-haloacetophenones, α-haloacetones, α-haloisopropyl phenyl ketones and the like; a halogen-substituted allyl compound such as allyl halides; a halogen-substituted nitrile compound such as 2-halopropionitriles and the like; a halogen-substituted carboxylic acid ester such as p-toluenesulfonyl halides, 4-methoxybenzenesulfonyl halides, methanesulfonyl halides, halomethanesulfonyl halides, dihalomethanesulfonyl halides, trihalomethanesulfonyl halides and the like; and the like.

Specific examples of the organic halogen compound having two halogen atoms include a halogen-substituted ketone such as 2,2-dihaloacetophenones, 1,1-dihaloacetones and the like; a halogen-substituted carboxylic acid ester such as ethylenebis(2-haloisobutyrates), 1,1,1-tris(2-haloisobutyryloxymethyl)ethanes, tetrakis(2-haloisobutyryloxymethyl)methanes and the like; and the like.

In the polymerization initiator to be used in the present invention, the blending molar ratio of the halogenocyclopentadienyl triorganophosphine $\eta^2$-olefin ruthenium complex represented by general formula (6) and the organic halide is preferably in such a range that the ratio of the ruthenium complex to the organic halide (ruthenium complex/organic halide) is 0.0001 to 1, because, too small a content of the latter results in slow polymerization rate while too large a content of the latter is broadens the molecular weight distribution.

In the method for producing the conjugated diene polymer of the present invention, an organic amine or a metal alkoxide can be used as an additive (activator) for accelerating the polymerization. When an organic amine or a metal alkoxide is used, the polymerization is accelerated to facilitate the production of the conjugated diene polymer of the present invention.

Specific examples of the organic amine include aliphatic amines including an aliphatic primary amine such as methylamine, ethylamine, propylamine, isopropylamine, butylamine and the like, an aliphatic secondary amine such as dimethylamine, diethylamine, dipropylamine, diisopropylamine, dibutylamine and the like, and an aliphatic tertiary amine such as trimethylamine, triethylamine, tripropylamine, triisopropylamine, tributylamine, N,N-dimethylaminoethanol and the like, and the like; an aliphatic polyamine such as N,N,N',N'-tetramethylethylenediamine, N,N,N',N'',N''-pentamethyldiethylenetriamine, 1,1,4,7,10,10-hexamethyltriethylenetetramine and the like; aromatic amines including an aromatic primary amine such as aniline, toluidine and the like; an aromatic secondary amine such as diphenylamine, and an aromatic tertiary amine such as triphenylamine, and the like; and the like. Among these, aliphatic amines are preferably used, and among them, butylamine, dibutylamine, or tributylamine is especially preferably used. These organic amines may be used either singly or in combination of two or more thereof.

Specific examples of the metal alkoxide include an aluminum trialkoxide such as aluminum triisopropoxide, aluminum tri(t-butoxide) and the like; a bis(substituted aryloxy)alkylaluminum such as bis(2,6-di-t-butylphenoxy)methylaluminum, bis(2,4,6-tri-t-butylphenoxy)methylaluminum and the like; a tris(substituted aryloxy)aluminum such as tris(2,6-diphenylphenoxy)aluminum and the like; a titanium tetraalkoxide such as titanium tetraisopropoxide and the like; and the like.

Among these, an aluminum trialkoxide and a titanium tetraalkoxide are preferred. Among them, aluminum triisopropoxide and titanium tetraisopropoxide are especially preferred. These metal alkoxide compounds may be used either singly or in combination of two or more thereof.

In the case where the blending molar ratio of the activator (an organic amine or a metal alkoxide) to the organic halide is too small, the polymerization rate becomes slow, and in the case where the blending molar ratio is too large, the processing after the polymerization reaction becomes complicated. Hence, the amount of the activator (an organic amine or a metal alkoxide) used is preferably in such a range that the ratio of the activator to the organic halide (activator/organic halide) is 0.01 to 100.

In the method for producing the conjugated diene polymer of the present invention, a phosphine compound may be added as a stabilizer to the polymerization system.

The addition of the phosphine compound permits efficient and reproducible realization of the method for producing the conjugated diene polymer of the present invention.

Examples of the phosphine compound includes, for example, a trialkylphosphine such as triethylphosphine, tributylphosphine and the like; a triarylphosphine such as triphenylphosphine, tri(m-tolyl)phosphine, tri(4-methoxyphenyl)phosphine, tri(p-trifluoromethylphenyl)phosphine, trinaphthylphosphine and the like; a trialkylphosphite such as tributylphosphite and the like; a triarylphosphite such as triphenylphosphite and the like; a bisphosphinoalkane such as 1,2-bis(diphenylphosphino)ethane and the like; a phosphaalkene; and the like. Among these, a triarylphosphine is preferred. These phosphine compounds may be used either singly or in combination of two or more thereof.

When the amount of the stabilizer used is too small, the effect as a stabilizer is not obtained, and when the amount is too large, the polymerization rate becomes slow. Hence, the amount of the stabilizer is preferably in such a range that the blending molar ratio of the stabilizer to the halogenocyclopentadienyl triorganophosphine $\eta^2$-olefin ruthenium complex represented by general formula (6) (stabilizer/ruthenium complex) is 0.01 to 100.

In the method for producing the conjugated diene polymer of the present invention, a radical generator may be added to accelerate the polymerization. Examples of the radical generators include, for example, an azo compound, an organic peroxide, a nonpolar radical generator and the like.

Specific examples of the azo compound include, for example, 2,2'-azobisisobutyronitrile, 2,2'-azobis-2-methylbutyronitrile, 2,2'-azobis-2,4-dimethylvaleronitrile, 1,1'-azobis-1-cyclohexanecarbonitrile, dimethyl-2,2'-azobisisobutyrate, 4,4'-azobis-4-cyanovaleric acid, 2,2'-azobis(2-amidinopropane)dihydrochloride, 2,2'-azobis(4-methoxy-2,4-dimethylvaleronitrile), 1-((1-cyano-1-metylethyl)azo)formamide, and the like.

Specific examples of the organic peroxide include hydroperoxides such as t-butyl hydroperoxide, p-menthane hydroperoxide, cumene hydroperoxide and the like; dialkylperoxides such as dicumylperoxide, t-butylcumylperoxide, α,α'-bis(t-butylperoxy-m-isopropyl)benzene, di-t-butylperoxide, 2,5-dimethyl-2,5-di(t-butylperoxide)-3-hexyne, 2,5-dimethyl-2,5-di(t-butylperoxide)hexane and the like; diacylperoxides such as dipropionylperoxide, benzoylperoxide and the like; peroxyketals such as 2,2-di(t-butylperoxy)butane, 1,1-di(t-hexylperoxy)cyclohexane, 1,1-di(t-butylperoxy)-2-methylcyclohexane, 1,1-di(t-butylperoxy)cyclohexane and the like; peroxyesters such as t-butylperoxyacetate, t-butylperoxybenzoate and the like; peroxycarbonates such as t-butylperoxyisopropylcarbonate, di(isopropylperoxy)dicarbonate and the like; alkylsilylperoxides such as t-butyltrimethylsilylperoxide and the like; cyclic peroxides such as 3,3,5,7,7-pentamethyl-1,2,4-trioxepane, 3,6,9-triethyl-3,6,9-trimethyl-1,4,7-triperoxonane, 3,6-diethyl-3,6-dimethyl-1,2,4,5-tetroxane and the like; and the like.

Specific examples of the nonpolar radical initiator include 2,3-dimethyl-2,3-diphenylbutane, 3,4-dimethyl-3,4-diphenylhexane, 1,1,2-triphenylethane, 1,1,1-triphenyl-2-phenylethane, and the like.

These radical generators may be used either singly or in combination of two or more thereof.

In the case where the radical generator is added, the proportion occupied by a polymer chain bearing a halogen atom at a terminal thereof (proportion relative to the total number of polymer chains) among all polymer chains-in all polymers constituting the conjugated diene polymer-obtained in the method for producing the conjugated diene polymer of the present invention is not particularly limited but is preferably 10% or higher, more preferably 15% or higher, even more preferably 20% or higher, most preferably 30% or higher.

The polymerization reaction in the method for producing the conjugated diene polymer of the present invention can be carried out in the absence of a solvent or in various solvents. Examples of the solvents to be used include hydrocarbon solvents such as benzene, toluene and the like; ether solvents such as diethyl ether, tetrahydrofuran, diphenyl ether, anisole, dimethoxybenzene and the like; halogenated hydrocarbon solvents such as methylene chloride, chloroform, chlorobenzene and the like; ketone solvents such as acetone, methyl ethyl ketone, methyl isobutyl ketone and the like; alcohol solvents such as methanol, ethanol, propanol, isopropanol, n-butanol, tert-butanol and the like; nitrile solvents such as acetonitrile, propionitrile, benzonitrile and the like; linear ester solvents such as ethyl acetate, butyl acetate and the like; cyclic ester solvents such as γ-butyrolactone, ε-caprolactone and the like; cyclic carbonate solvents such as ethylene carbonate, propylene carbonate and the like; amide solvents such as N,N-dimethylformamide, N-methylpyrrolidone and the like; sulfoxide solvents such as dimethyl sulfoxide and the like; and the like. Among these, cyclic ester solvents such as γ-butyrolactone, ε-caprolactone and the like are preferred for the following reason as when these solvents are used, the polymerization reaction is accelerated. These solvents may be used either singly or in combination of two or more thereof.

In the method for producing the conjugated diene polymer of the present invention, the method of preparing a polymerization initiator is not particularly limited. However, it is preferred to prepare a mixture comprising a monomer, a solvent, various additives (an activator, a stabilizer and a radical generator) and a halogenocyclopentadienyl triorganophosphine $\eta^2$-olefin ruthenium complex represented by general formula (6) under an inert gas atmosphere such as nitrogen in a reaction vessel followed by addition of an organic halide thereto. The polymerization can be initiated, for example, by heating the thus obtained mixture to a temperature within the range of from 40° C. to 120° C.

In the method for producing the conjugated diene polymer of the present invention, the initial concentration of the monomer containing at least a conjugated diene in the polymerization system is not necessarily limited. However, in the case where the concentration is too low, the reaction rate is too slow, and in the case where the concentration is too high, a chain transfer reaction of formed radicals to a monomer is increased and there is a tendency to result in a wide molecular weight distribution of the polymer obtained. Therefore, the concentration is preferably in the range of from 0.5 to 8 mol/L.

The concentration in the polymerization system of the respective ingredients to be used for the polymerization is not necessarily limited, but the concentration the organic halide is preferably in the range of from 0.5 to 50 mmol/L, although it varies depending on the concentration of the monomer. The concentration of the halogenocyclopentadienyl triorganophosphine $\eta^2$-olefin ruthenium complex represented by general formula (6) is preferably in the range of from 0.00005 to 50 mmol/L. The concentration of the activator (an organic amine or a metal alkoxide) is preferably in the range of from 0.000005 to 5,000 mmol/L.

The conjugated diene polymer of the present invention can be blended with a vulcanizing agent to give a vulcanizable composition followed by vulcanization (crosslinking) molding of the composition to be formed into a vulcanized molded body having excellent mechanical strength.

As a vulcanizing agent, a vulcanizing agent used usually as a vulcanizing agent for the conjugated polymer can be used. Examples of such a vulcanizing agent include a sulfur-based vulcanizing agent and an organic peroxide vulcanizing agent. In the case where the conjugated polymer is a copolymer of a conjugated diene and other monomer, a vulcanizing agent for crosslinking the copolymerized monomer can be also used. The blending amount of the vulcanizing agent is not particularly limited.

Specific examples of the sulfur-based vulcanizing agent include sulfur such as powdery sulfur, sublimed sulfur, precipitated sulfur, colloidal sulfur, surface-treated sulfur, insoluble sulfur and the like; sulfur-containing compounds such as sulfur chloride, sulfur dichloride, morpholine disulfide, alkylphenol disulfide, N,N'-dithio-bis(hexahydro-2H-azenopin-2), phosphorus-containing polysulfide, and polymeric polysulfide; sulfur-donating compounds such as tetramethylthiuram disulfide, selenium dimethyldithiocarbamate, 2-(4'-morpholinodithio)benzothiazole and the like; and the like.

In the case when the sulfur-based vulcanizing agent is used as a vulcanizing agent, auxiliaries such as zinc white, stearic acid and the like; vulcanization accelerators such as guanidine-based, aldehyde-amine-based, aldehyde-ammonia-based, thiazole-based, sulfenamide-based, thiourea-based vulcanization accelerators and the like; and the like can be used in combination with vulcanization. The used amount of these vulcanization auxiliaries and vulcanization accelerators is not particularly limited.

Specific examples of the organic peroxide vulcanizing agent include, for example, hydroperoxides such as cumene hydroperoxide and the like; dialkylperoxides such as dicumylperoxide, t-butylcumylperoxide, 1,3-bis(t-butylperoxyisopropyl)benzene, 1,4-bis(t-butylperoxyisopropyl)benzene, di-t-butylperoxide, 2,5-dimethyl-2,5-di-t-butylperoxy-3-hexyne, 2,5-dimethyl-2,5-di-t-butylperoxyhexane and the like; diacylperoxides such as p-chlorobenzoylperoxide and the like; peroxyketals such as 4,4-bis-(t-butylperoxy)-n-butylvalerate, 1,1-di-t-butylperoxy-3,5,5-trimethylcyclohexane, 1,1-di-t-butylperoxy-3,3,5-trimethylcyclohexane and the like; peroxyesters such as t-butylperoxyacetate, t-butylperoxybenzoate and the like; peroxycarbonates such as t-butylperoxyisopropylcarbonate and the like; and the like.

In the case when the organic peroxide vulcanizing agent is used as a vulcanizing agent, multifunctional monomers such as trimethylolpropane trimethacrylate, divinylbenzene, ethylene dimethacrylate, triallyl isocyanurate and the like can be used as vulcanization auxiliaries. The used amount of these vulcanization auxiliaries is not particularly limited.

EXAMPLES

Hereinbelow, the present invention will be explained in more detail by reference to Examples and Comparative Examples. All the parts and % in the respective Examples are by weight unless specifically indicated otherwise.

The weight-average molecular weight (Mw), the number-average molecular weight (Mn), and polydispersity (Mw/Mn) in terms of polystyrene of the polymer in the respective Examples were determined by a gel permeation chromatography (GPC) method using tetrahydrofuran (THF) as an effluent with Shodex KF400RL and KF400RH columns (polystyrene gel) manufactured by Showa Denko K.K.

The polymerization conversion rate of a monomer, the ratio of a polymer bearing a halogen atom at a terminal of a polymer chain, the molecular weight of a polymer by a NMR measurement were calculated on the basis of $^1$H-NMR measurement using JNM-LA500 manufactured by JEOL Ltd. as a measuring apparatus and $CDCl_3$ as a solvent. The proportion of the terminal structure of a polymer bearing a halogen atom at the terminal of a polymer chain was calculated by measuring the number of protons on the carbon bonded with halogen on the basis of the number of the protons of the organic groups derived from the organic halide used.

Synthesis Example 1

Figure 4:
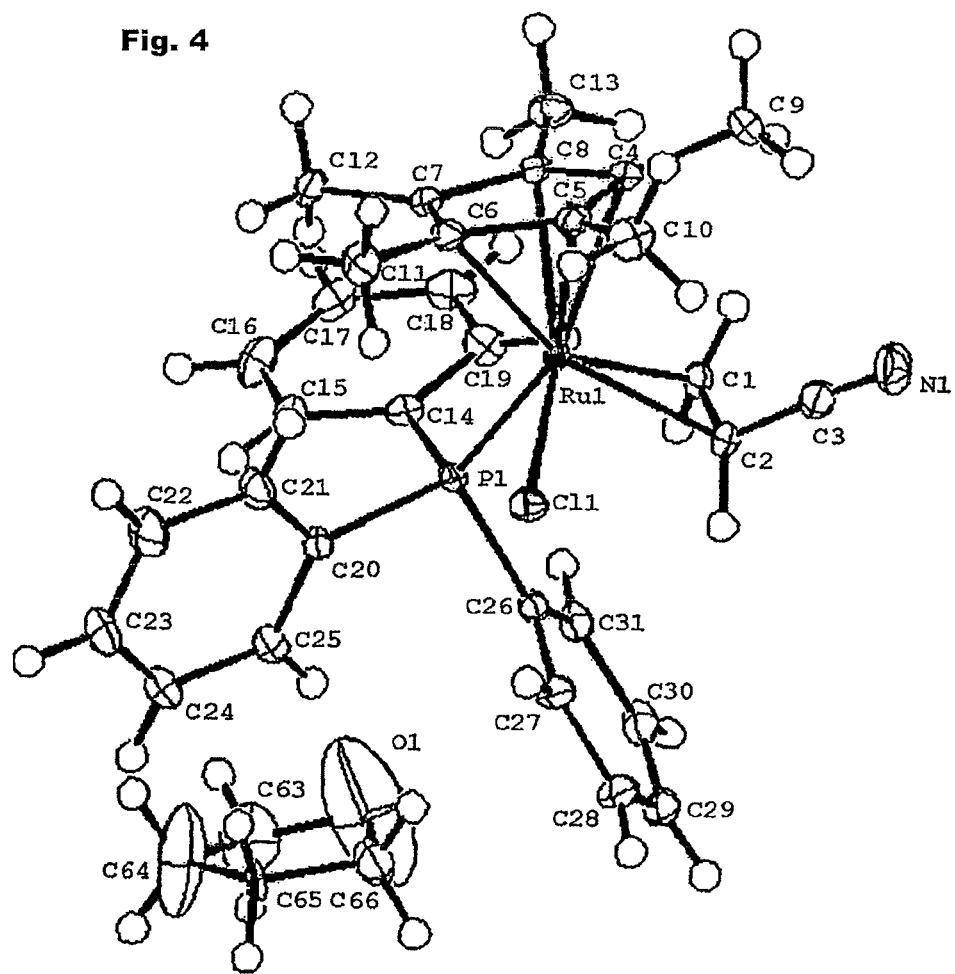
FIG. 4 is a presentation showing an ORTEP (Oak Ridge Thermal Ellipsoid Plot) according to single crystal X-ray structure analysis of a chloropentamethylcyclopentadienyl triphenylphosphine $\eta^2$-acrylonitrile ruthenium complex synthesized in Synthesis Example 1.

Synthesis of Chloropentamethylcyclopentadienyl Triphenylphosphine $\eta^2$-Acrylonitrile Ruthenium Under nitrogen atmosphere, 1.59 parts of chloropentamethylcyclopentadienyl bistriphenylphosphine ruthenium (manufactured by Sigma-Aldrich Co.) (this complex corresponds to the compound of general formula (11) in which $R^{19}$ is a chlorine atom, $R^{20}$ to $R^{25}$ all are a phenyl group, and L is a pentamethylcyclopentadienyl ring, and, hereinafter, referred to as "Ru complex (11a)") and 88 parts of toluene were introduced into a 30 mL glass reaction vessel and heated to 80° C. to dissolve the ruthenium catalyst. Then, 0.53 part of acrylonitrile was added thereto, and the mixture was stirred for 3 hours at room temperature. Subsequently, the volatiles were distilled off under reduced pressure, and the obtained residue was re-precipitated from 100 parts of hexane. After filtration, the volatiles were distilled off under reduced pressure to give a complex. The complex obtained was recrystallized from hexane, and the crystal obtained was subjected to single-crystal X-ray structure analysis. Consequently, as shown in FIG. 4, the complex was identified as chloropentamethylcyclopentadienyl triphenylphosphine $\eta^2$-acrylonitrile ruthenium (hereinafter, referred to as "the ruthenium complex (A)").

Synthesis Example 2 (Example)

Synthesis of Chloropentamethylcyclopentadienyl Triphenylphosphine $\eta^2$-Fumaronitrile Ruthenium Under nitrogen atmosphere, 1.59 parts of chloropentamethylcyclopentadienyl bistriphenylphosphine ruthenium (manufactured by Sigma-Aldrich Co.) and 88 parts of toluene were introduced into a 30 mL glass reaction vessel and heated to 80° C. to dissolve the ruthenium catalyst. Then, 0.78 part of fumaronitrile was added thereto, and the mixture was stirred for 3 hours at room temperature. Subsequently, the volatiles were distilled off under reduced pressure, and the obtained residue was re-precipitated from 100 parts of hexane. After filtration, the volatiles were distilled off under reduced pressure to give a complex. The complex obtained was recrystallized from THF/hexane to give a crystal.

Figure 5:
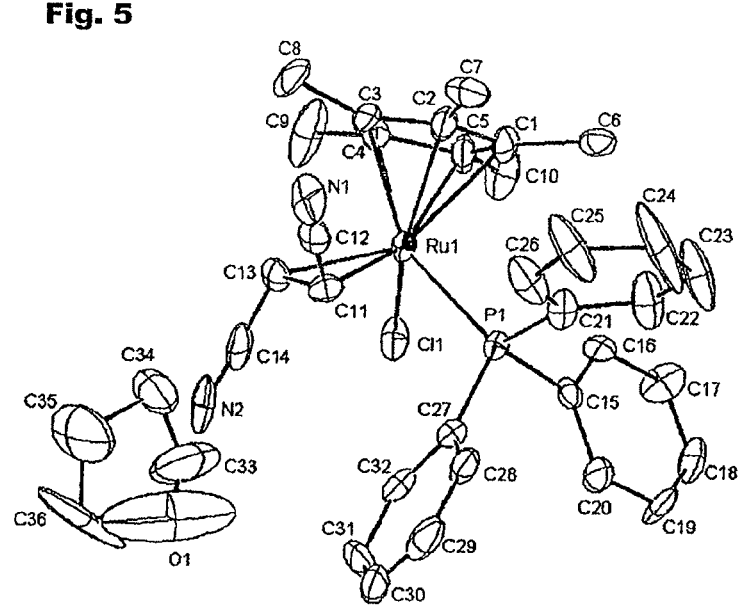
FIG. 5 is a presentation showing an ORTEP (Oak Ridge Thermal Ellipsoid Plot) according to single crystal X-ray structure analysis of a chloropentamethylcyclopentadienyl triphenylphosphine $\eta^2$-fumaronitrile ruthenium complex synthesized in Synthesis Example 3 (in Examples).

The crystal obtained was subjected to $^1$H-NMR measurement, $^{13}$C-NMR measurement, and single-crystal X-ray structure analysis. From the results of the $^1$H-NMR measurement ($^1$H-NMR (heavy toluene, 500 MHz): δ=7.71-6.89 (m, 15H), 2.99 (dd, J=15.0, 9.5 Hz, 1H), 2.90 (dd, J=9.5, 2.0 Hz, 1H), 1.07 (d, J=1.5 Hz, 15H)) and the $^{13}$C-NMR measurement ($^{13}$C-NMR (heavy toluene, 100 MHz): δ=136.2, 133.9, 131-129, 123.3, 119.2, 99.5, 28.5, 24.3, 7.8) and the ORTEP diagram of FIG. 5 to be identified as chloropentamethylcyclopentadienyl triphenylphosphine $\eta^2$-fumaronitrile ruthenium (hereinafter, referred to as "the ruthenium complex (B)").

This complex is a novel compound.

Synthesis Example 3

Synthesis of Chloropentamethylcyclopentadienyl Triphenylphosphine η2-Methyl Vinyl Ketone Ruthenium Under nitrogen atmosphere, 1.59 parts of chloropentamethylcyclopentadienyl bistriphenylphosphine ruthenium (manufactured by Sigma-Aldrich Co.) and 88 parts of toluene were introduced into a 30 mL glass reaction vessel and heated to 80° C. to dissolve the ruthenium catalyst. Then, 0.70 part of methyl vinyl ketone was added thereto, and the mixture was stirred for 3 hours at room temperature. Subsequently, the volatiles were distilled off under reduced pressure, and the obtained residue was re-precipitated from 100 parts of hexane. After filtration, the volatiles were distilled off under reduced pressure to give a complex. The complex obtained was subjected to NMR measurement to be identified as chloropentamethylcyclopentadienyl triphenylphosphine $\eta^2$-methyl vinyl ketone ruthenium (hereinafter, referred to as "the ruthenium complex (C)").

Synthesis Example 4

Synthesis of Bromopentamethylcyclopentadienyl Bistriphenylphosphine Ruthenium

Under nitrogen atmosphere, 0.3 part of chloropentamethylcyclopentadienyl bistriphenylphosphine ruthenium (manufactured by Sigma-Aldrich Co.) (ruthenium complex (11a)), 2.466 parts of potassium bromide (manufactured by Wako Pure Chemical Industries, Ltd.), and 60 parts of ethanol were introduced into a 100 mL glass reaction vessel provided with a cooling tube, and the mixture was refluxed under heating for 72 hours. Subsequently, after cooling to room temperature, the volatiles were distilled off under reduced pressure, and the obtained residue was washed with deaerated water and then dried under reduced pressure to give a complex. The complex obtained was subjected to $^1$H-NMR measurement to be identified as bromopentamethylcyclopentadienyl bistriphenylphosphine ruthenium (RuCp*Br(PPh$_3$)$_2$) (hereinafter, in the Examples, referred to as "ruthenium complex (11b)").

Example 1

Under nitrogen atmosphere, 1.17 parts of the ruthenium complex (A) obtained in Synthesis Example 1, 263 parts of toluene as a solvent, 2.58 parts of dibutylamine as an activator, and 17.3 parts of hexane as an internal standard for NMR measurement (hereinafter, referred to merely as "internal standard") were introduced into a 30 mL glass reaction vessel and heated to 80° C. to dissolve the ruthenium complex (A).

Then, thereto were added 53.0 parts of acrylonitrile, 68.2 parts of isoprene and 3.70 parts of methyl α-chlorophenyl acetate as an organic halide, and the mixture was stirred under heating at 80° C. After 142 hours, the glass reaction vessel was cooled in a dry ice-methanol bath, and the volatiles were distilled off under reduced pressure to give a random (isoprene/acrylonitrile) copolymer. After completion of the polymerization reaction, the conversion rate of isoprene was 89% and the conversion rate of acrylonitrile was 84%. The molecular weight in terms of polystyrene of the random (isoprene/acrylonitrile) copolymer obtained was Mw=2,990, Mn=1,920, and Mw/Mn=1.56. From the results of the $^1$H-NMR analysis of the random (isoprene/acrylonitrile) copolymer obtained, the polymer was confirmed to have 3% (the proportion of the number of polymer chains relative to the total polymer chains, the same shall apply hereinafter) of the structures represented by formulae (13a) and (13b), which are classified into general formula (1), 24% of the structure represented by formula (14), which is classified into general formula (2), and 64% of the structure represented by formula (15), which is classified into general formula (3), and a chlorine atom at one terminal of the polymer chain.

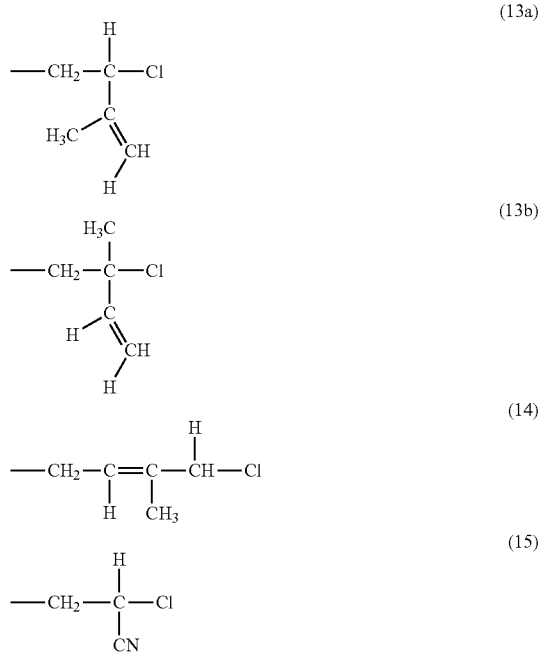

Figure 2A:
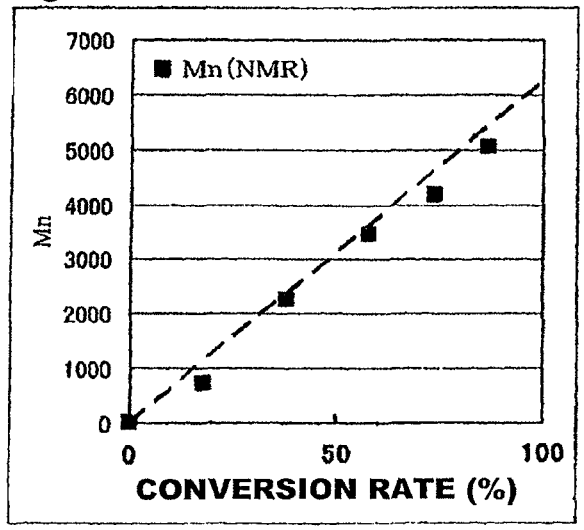
FIG. 2A is a graph showing a correlation between the monomer conversion rate and the molecular weight based on the NMR measurement of the polymer, each of which changed with the passage of time in the reaction system during the polymer production in Example 1.
Figure 2B:
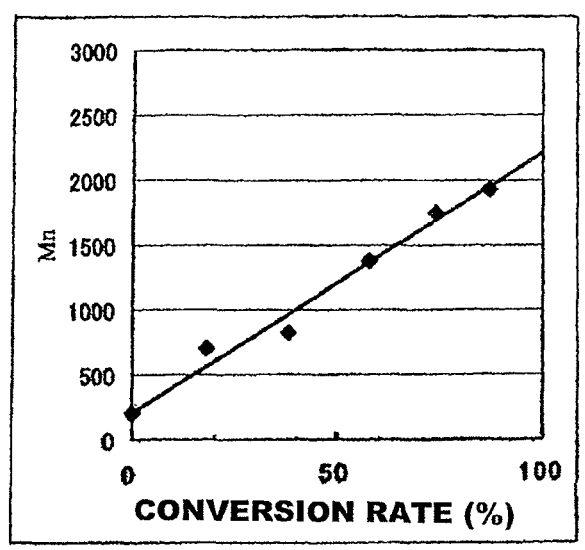
FIG. 2B is a graph showing a correlation between the monomer conversion rate and the number-average molecular weight in terms of polystyrene based on the GPC measurement of the polymer, each of which changed with the passage of time in the reaction system during the polymer production in Example 1.
Figure 3:
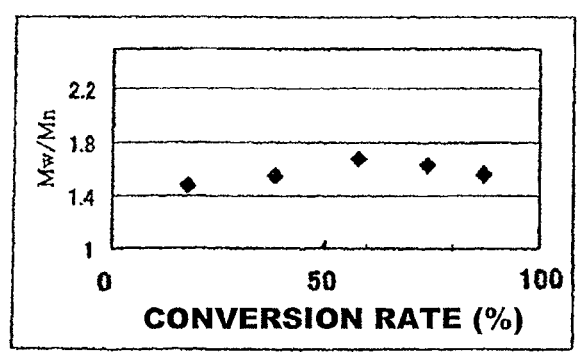
FIG. 3 is a graph showing a correlation between the monomer conversion rate and the polydispersity of the polymer, each of which changed with the passage of time in the reaction system during the polymer production in Example 1.

During the polymerization reaction, samples were taken out of the reaction system at a prescribed time interval, and the molecular weight of the polymer and the monomer conversion rate in the polymerization reaction system were measured. On the basis of these results, there were obtained a chart of gel permeation chromatography (GPC) showing changes with the passage of time of the molecular weight in terms of polystyrene of the polymer in the reaction system (FIG. 1), a graph showing a correlation between a monomer conversion rate and an absolute molecular weight of the polymer, each changing with the passage of time in the reaction system (FIG. 2A), a graph showing a correlation between a monomer conversion rate and a number-average molecular weight in terms of polystyrene of the polymer, each changing with the passage of time in the reaction system (FIG. 2B), and a graph showing a correlation between a monomer conversion rate and polydispersity (Mw/Mn) of the polymer, each changing with the passage of time in the reaction system (FIG. 3). In FIG. 1, the horizontal axis represents a retention time in GPC, the vertical axis represents intensity, and A, B and C each represent GPC curve after 10 hours, 70 hours, and 142 hours, respectively from the initiation of polymerization. In FIG. 2A, the dotted line represents a theoretical Mn. From these figures, it can be seen that the polymerization reaction proceeded with high living characteristics.

Example 2

Under nitrogen atmosphere, 1.27 parts of the ruthenium complex (A), 263 parts of toluene, 3.71 parts of tributylamine as an activator, 2.62 parts of triphenylphosphine as a stabilizer, and 17.3 parts of hexane as an internal standard were introduced into a 30 mL glass reaction vessel, and heated to 80° C. to dissolve the ruthenium complex (A).

Then, were added thereto 136.0 parts of isoprene and 3.62 parts of methyl-2-bromoisobutyrate as an organic halide, and stirred under heating at 100° C. to polymerize. After 113 hours, the same post-treatment as in Example 1 was carried out to give polyisoprene. The conversion rate of isoprene was 67%. The analysis results of the polyisoprene polymer obtained are shown in Table 1. The polymer was confirmed to have a bromine atom at one terminal of the polymer chain.

Example 3

A polymerization was carried out in the same manner as in Example 2, except that triphenylphosphine as a stabilizer was not added, that 86.1 parts of methyl acrylate and 68.2 parts of isoprene were used as a monomer in place of 136.0 parts of isoprene, and that the reaction temperature was changed to 80° C. After 186 hours, the same post-treatment as in Example 1 was carried out to give a random (isoprene/methyl acrylate) copolymer. The conversion rate of isoprene was 90% and the conversion rate of methyl acrylate was 85%. The molecular weight in terms of polystyrene of the random (isoprene/methyl acrylate) polymer obtained was Mw=2,070, Mn=1,380, and Mw/Mn=1.50. The polymer was confirmed to have 3% of the structure represented by general formula (1), 30% of the structure represented by general formula (2), and 53% of the structure represented by formula (16), which is classified into general formula (3), relative to the total polymer chains, respectively, and a bromine atom at one terminal of the polymer chain.

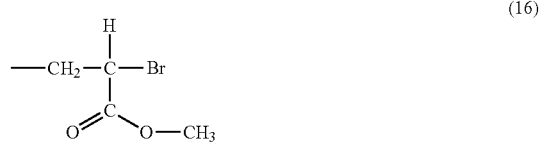

TABLE 1

|  | EXAMPLE | | | |
|---|---|---|---|---|
|  | 1 | 2 | 3 | 4 |
| Ruthenium complex as a polymerization catalyst | Complex(A) | Complex(A) | Complex(A) | Complex(A) |
| Amount used (parts) | 1.17 | 1.27 | 1.27 | 1.27 |
| Polymerization solvent | TOL | TOL | TOL | TOL |
| Amount used (parts) | 263 | 263 | 263 | 263 |
| Activator |  |  |  |  |
| Amine | DBA | TBA | TBA | TBA |
| Amount used (parts) | 2.58 | 3.71 | 3.71 | 3.71 |
| Stabilizer | . . . | PPh3 | . . . | . . . |
| Amount used (parts) | . . . | 2.62 | . . . | . . . |
| Internal standard | HX | HX | HX | HX |
| Amount used (parts) | 17.3 | 17.3 | 17.3 | 17.3 |
| Polymerization Monomer |  |  |  |  |
| Conjugated diene | IP | IP | IP | IP |
| Amount used (parts) | 68.2 | 136.0 | 68.2 | 68.2 |
| Comonomer | AN | . . . | MA | MMA |
| Amount used (parts) | 53.0 | . . . | 86.1 | 100.1 |
| Organic halide | MCPA | MBIB | MBIB | MBIB |
| Amount used (parts) | 3.70 | 3.62 | 3.62 | 3.62 |
| Reaction temperature | 80° C. | 100° C. | 80° C. | 80° C. |
| Reaction time | 142 h | 113 h | 186 h | 186 h |
| Polymer | Random (IP-AN) copolymer | IP Homopolymer | Random (IP-MA) copolymer | Random (IP-MMA) copolymer |
| Conjugated diene conversion rate (%) | 89 | 67 | 90 | 62 |
| Comonomer conversion rate (%) | 84 | . . . | 85 | 38 |
| Weight-average molecular weight | 2,990 | 11,670 | 2,070 | 9,200 |
| Number-average molecular weight | 1,920 | 5,890 | 1,380 | 5,600 |
| Mw/Mn | 1.56 | 1.98 | 1.50 | 1.64 |
| Ratio (%) of polymer chains having a halogen atom at the terminal |  |  |  |  |
| Terminal group structure (1) | 3 | 6 | 3 | 6 |
| Terminal group structure (2) | 24 | 60 | 30 | 56 |
| Terminal group structure (3) | 64 | . . . | 53 | 21 |
| TOTAL | 91 | 66 | 86 | 83 |

Example 4

A polymerization reaction was carried out in the same manner as in Example 3, except that the monomer was changed to 100.1 parts of methyl methacrylate and 68.2 parts of isoprene. After 186 hours, the same post-treatment as in Example 1 was carried out to give a random (isoprene/methyl methacrylate) copolymer. The conversion rate of isoprene was 62% and the conversion rate of methyl methacrylate was 38%. The molecular weight in terms of polystyrene of the random (isoprene/methyl methacrylate) copolymer obtained was Mw=9,200, Mn=5,600, and Mw/Mn=1.64. The polymer was confirmed to have 6% of the structure represented by general formula (1), 56% of the structure represented by general formula (2), and 21% of the structure represented by formula (17), which is classified into general formula (3), relative to the total polymer chains, respectively, and a bromine atom at one terminal of the polymer chain.

Example 5

A polymerization reaction was carried out in the same manner as in Example 20, except that the monomer was changed to 104.2 parts of styrene and 68.2 parts of isoprene to give a random (isoprene/styrene) copolymer. The conversion rate of isoprene was 48% and the conversion rate of styrene was 45%. The molecular weight in terms of polystyrene of the random (isoprene/styrene) copolymer obtained was Mw=9,010, Mn=5,510, and Mw/Mn=1.64. The polymer was confirmed to have 4% of the structure represented by general formula (1), 41% of the structure represented by general formula (2), and 35% of the structure represented by formula (18), which is classified into general formula (3), relative to all polymer chains, respectively, and a bromine atom at one terminal of the polymer chain.

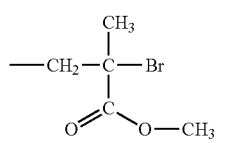

(17)

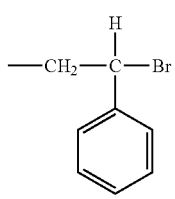

(18)

TABLE 2

| | EXAMPLE | | |
|---|---|---|---|
| | 5 | 6 | 7 |
| Ruthenium complex as a polymerization catalyst | Complex(A) | Complex(B) | Complex(C) |
| Amount used (parts) | 1.27 | 1.28 | 1.27 |
| Polymerization solvent | TOL | TOL | TOL |
| Amount used (parts) | 263 | 263 | 263 |
| Activator | | | |
| Amine | TBA | TBA | TBA |
| Amount used (parts) | 3.71 | 3.71 | 3.71 |
| Stabilizer | ... | ... | ... |
| Amount used (parts) | ... | ... | ... |
| Internal standard | HX | HX | HX |
| Amount used (parts) | 17.3 | 17.3 | 17.3 |
| Polymerization Monomer | | | |
| Conjugated diene | IP | IP | IP |
| Amount used (parts) | 68.2 | 68.2 | 68.2 |
| Comonomer | ST | AN | MA |
| Amount used (parts) | 104.2 | 53.0 | 86.1 |
| Organic halide | MBIB | MCPA | MBIB |
| Amount used (parts) | 3.62 | 3.7 | 3.62 |
| Reaction temperature | 80° C. | 80° C. | 80° C. |
| Reaction time | 186 h | 142 h | 142 h |
| Polymer | Random (IP-ST) copolymer | Random (IP-AN) copolymer | Random (IP-MA) copolymer |
| Conjugated diene conversion rate (%) | 48 | 63 | 86 |
| Comonomer conversion rate (%) | 45 | 56 | 77 |
| Weight-average molecular weight | 9,010 | 5,300 | 2,850 |
| Number-average molecular weight | 5,510 | 3,220 | 1,680 |
| Mw/Mn | 1.64 | 1.65 | 1.70 |
| Ratio (%) of polymer chains having a halogen atom at the terminal | | | |
| Terminal group structure (1) | 4 | 3 | 2 |
| Terminal group structure (2) | 41 | 23 | 27 |
| Terminal group structure (3) | 35 | 58 | 48 |
| TOTAL | 80 | 84 | 77 |

Example 6

A random (isoprene/acrylonitrile) copolymer was obtained in the same manner as in Example 1, except that 1.28 parts of ruthenium complex (B) obtained in Synthesis Example 2 was used in place of 1.17 parts of the ruthenium complex (A) and that 3.71 parts of tributylamine was used as an activator in the place of 2.58 parts of dibutylamine. The conversion rate of isoprene was 63% and the conversion rate of acrylonitrile was 56%. The analysis results of the random (isoprene/acrylonitrile) copolymer obtained are shown in Table 2. The polymer was confirmed to have a chlorine atom at one terminal of the polymer chain.

Example 7

Example in which the Ruthenium Complex (C) of Synthesis Example 3 was used

Chloropentamethylcyclopentadienyl Triphenylphosphine η²-Methyl Vinyl Ketone Ruthenium IP/MA Copolymer A polymerization reaction was carried out in the same manner as in Example 6, except that 1.27 parts of the ruthenium complex (C) obtained in Synthesis Example 3 was used in place of 1.17 parts of the ruthenium complex (A), that 3.62 parts of methyl 2-bromoisobutyrate was used as an organic halide in place of 3.70 parts of methyl α-chlorophenyl acetate, and that the monomer was changed to 86.1 parts of methyl acrylate and 68.2 parts of isoprene. After 142 hours, the same treatment as in Example 1 was carried out to give a random (isoprene/methyl acrylate) copolymer. The conversion rate of isoprene was 86% and the conversion rate of methyl acrylate was 77%. The molecular weight in terms of polystyrene of the random (isoprene/methyl acrylate) polymer obtained was Mw=2,850, Mn=1,680, and Mw/Mn=1.70. The polymer was confirmed to have 2% of the structure represented by general formula (1), 27% of the structure represented by general formula (2), and 48% of the structure represented by formula (14), which is classified into general formula (3), relative to the total polymer chains, respectively, and a bromine atom at one terminal of the polymer chain.

Example 8

Preparation of the Ruthenium Complex (A)

Under nitrogen atmosphere, 1.59 parts of Ru complex (11a), 263 parts of toluene as a solvent, 2.58 parts of dibutylamine as an activator and 17.3 parts of hexane as an internal standard were introduced into a 30 mL glass reaction vessel, and heated to 80° C. to dissolve Ru complex (11a). Then, was added thereto 53.0 parts of acrylonitrile as a complex-preparing raw material and monomer, followed by stirring at room temperature for 5 minutes to prepare the ruthenium complex (A) in the reaction system.

Polymerization by the Ruthenium Complex (A)

Then, were added thereto 68.2 parts of isoprene and 3.70 parts of methyl α-chlorophenyl acetate as an organic halide, and stirred under heating at 80° C. After 130 hours, the same post-treatment as in Example 1 was carried out to give a random (isoprene/acrylonitrile) copolymer. The conversion rate of isoprene was 88% and the conversion rate of acrylonitrile was 85%. The analysis results of the random (isoprene/acrylonitrile) polymer obtained are shown in Table 3. The polymer was confirmed to have a chlorine atom at the terminal of the polymer chain.

Example 9

Preparation of the Ruthenium Complex (A)

Under nitrogen atmosphere, 0.40 part of Ru complex (11a), 123 parts of toluene as a solvent, 0.65 part of dibutylamine as an activator, and 17.3 parts of hexane as an internal standard were introduced into a 30 mL glass reaction vessel, and heated to 80° C. to dissolve Ru complex (11a). Then, was added thereto 106 parts of acrylonitrile as a complex-preparing raw material and monomer, followed by stirring at room temperature for 5 minutes to prepare the ruthenium complex (A) in the reaction system.

Polymerization by the Ruthenium Complex (A)

Then, were added thereto 136 parts of isoprene and 0.37 part of methyl α-chlorophenyl acetate as an organic halide, and stirred under heating at 80° C. After a reaction for 17 hours, the same post-treatment as in Example 1 was carried out—to give a random (isoprene/acrylonitrile) copolymer. The conversion rate of isoprene was 31% and the conversion rate of acrylonitrile was 35%. The analysis results of the random (isoprene/acrylonitrile) polymer obtained are shown in Table 3. The polymer was confirmed to have a chlorine atom at the terminal of the polymer chain.

TABLE 3

| | EXAMPLE | | | | |
| --- | --- | --- | --- | --- | --- |
| | 8 | 9 | 10 | 11 | 12 |
| Raw material Ru complex | (11a) | (11a) | (11a) | (11a) | (11a) |
| Amount used (parts) | 1.59 | 0.4 | 1.59 | 1.59 | 1.59 |
| Ligand | AN | AN | AN | AN | AN |
| Amount used (parts) | 53.0 | 106.0 | 53.0 | 53.0 | 53.0 |
| Solvent for preparation of complex | TOL | TOL | TOL | TOL | TOL |
| Amount used (parts) | 263 | 123 | 263 | 263 | 263 |
| Ruthenium complex as a polymerization catalyst | Complex(A) | Complex(A) | Complex(A) | Complex(A) | Complex(A) |
| Activator | | | | | |
| Amine | DBA | DBA | TBA | BA | ... |
| Amount used (parts) | 2.58 | 0.65 | 3.71 | 1.46 | ... |
| Metal alkoxide | ... | ... | ... | ... | TTIP |
| Amount used (parts) | ... | ... | ... | ... | 5.68 |
| Internal standard | HX | HX | HX | HX | HX |
| Amount used (parts) | 17.3 | 17.3 | 17.3 | 17.3 | 17.3 |
| Polymerization Monomer | | | | | |
| Conjugated diene | IP | IP | IP | IP | IP |
| Amount used (parts) | 68.2 | 136.0 | 68.2 | 68.2 | 68.2 |
| Comonomer | AN | AN | AN | AN | AN |
| Amount used (parts) | (*1) | (*1) | (*1) | (*1) | (*1) |
| Organic halide | MCPA | MCPA | CPN | CPN | CPN |
| Amount used (parts) | 3.70 | 0.37 | 1.79 | 1.79 | 1.79 |
| Polymerization solvent | TOL | TOL | TOL | TOL | TOL |
| Amount used (parts) | (*1) | (*1) | (*1) | (*1) | (*1) |
| Reaction temperature | 80° C. | 80° C. | 80° C. | 80° C. | 80° C. |
| Reaction time | 130 h | 17 h | 137 h | 137 h | 137 h |
| Polymer | Random (IP-AN) copolymer | Random (IP-AN) copolymer | Random (IP-AN) copolymer | Random (IP-AN) copolymer | Random (IP-AN) copolymer |
| Conjugated diene conversion rate (%) | 88 | 31 | 84 | 90 | 95 |
| Comonomer conversion rate (%) | 85 | 35 | 79 | 85 | 83 |
| Weight-average molecular weight | 3,200 | 64,820 | 3,960 | 3,970 | 4,320 |

TABLE 3-continued

| | EXAMPLE | | | | |
|---|---|---|---|---|---|
| | 8 | 9 | 10 | 11 | 12 |
| Number-average molecular weight | 2,120 | 39,910 | 2,470 | 2,570 | 2,670 |
| Mw/Mn | 1.51 | 1.62 | 1.60 | 1.54 | 1.62 |
| Ratio (%) of polymer chains having a halogen atom at the terminal | | | | | |
| Terminal group structure (1) | 3 | 6 | 3 | 3 | 4 |
| Terminal group structure (2) | 24 | 54 | 25 | 24 | 36 |
| Terminal group structure (3) | 63 | 35 | 62 | 61 | 50 |
| TOTAL | 90 | 95 | 90 | 88 | 90 |

*1: Added on preparing the catalyst.

Example 10

Preparation of the Ruthenium Complex (A)

263 parts of toluene as a solvent, 3.71 parts of tributylamine as an activator and 17.3 parts of hexane as an internal standard were added to 1.59 parts of Ru complex (10a), and heated to 80° C. to dissolve Ru complex (10a). Then, was added thereto 53.0 parts of acrylonitrile as a complex-preparing raw material and monomer, followed by stirring at room temperature for 5 minutes to prepare the ruthenium complex (A) in the reaction system.

(Polymerization by the Ruthenium Complex (A))

Then, were added thereto 68.2 parts of isoprene and 1.79 parts of 2-chloropropionitrile as an organic halide and stirred under heating at 80° C. to conduct a polymerization reaction. After 137 hours, the same post-treatment as in Example 1 was carried out to give a random (isoprene/acrylonitrile) copolymer. The conversion rate of isoprene was 84% and the conversion rate of acrylonitrile was 79%. The analysis results of the random (isoprene/acrylonitrile) polymer obtained are shown in Table 3. The polymer was confirmed to have a chlorine atom at the terminal of the polymer chain.

Example 11

The ruthenium complex (A) was prepared in the same manner as in Example 10, except that 1.46 parts of butylamine was used as an activator in place of 3.71 parts of tributylamine, and a polymerization reaction was carried out using the ruthenium complex (A). The conversion rate of isoprene was 90% and the conversion rate of acrylonitrile was 85%. The analysis results of the random (isoprene/acrylonitrile) polymer obtained are shown in Table 3. The polymer was confirmed to have a chlorine atom at the terminal of the polymer chain.

Example 12

The ruthenium complex (A) was prepared in the same manner as in Example 10, except that 5.68 parts of titanium tetraisopropoxide was used as an activator in place of 3.71 parts of tributylamine, and a polymerization reaction was carried out using the ruthenium complex (A). The conversion rate of isoprene was 95% and the conversion rate of acrylonitrile was 83%. The analysis results of the random (isoprene/acrylonitrile) polymer obtained are shown in Table 3. The polymer was confirmed to have a chlorine atom at the terminal of the polymer chain.

Example 13

The ruthenium complex (A) was prepared in the same manner as in Example 10, except that 3.62 parts of methyl 2-bromoisobutyrate was used as an organic halide in place of 1.79 parts of 2-chloropropionitrile, and a polymerization reaction was carried out using the ruthenium complex (A). The conversion rate of isoprene was 82% and the conversion rate of acrylonitrile was 75%. The analysis results of the random (isoprene/acrylonitrile) polymer obtained are shown in Table 4. The polymer was confirmed to have a bromine atom at the terminal of the polymer chain.

Example 14

The ruthenium complex (A) was prepared in the same manner as in Example 13, except that the amount of tributylamine as an activator was changed to 37.1 parts, and a polymerization reaction was carried out using the ruthenium complex (A). After 112 hours, the same post-treatment as in Example 1 was carried out to give a random (isoprene/acrylonitrile) copolymer. The conversion rate of isoprene was 74% and the conversion rate of acrylonitrile was 71%. The analysis results of the random (isoprene/acrylonitrile) polymer obtained are shown in Table 4. The polymer was confirmed to have a bromine atom at the terminal of the polymer chain.

Example 15

The ruthenium complex (A) was prepared in the same manner as in Example 10, except that 4.56 parts of ethyl 2-iodopropionate was used as an organic halide in place of 1.79 parts of 2-chloropropionitrile, and a polymerization reaction was carried out using the ruthenium complex (A). After 137 hours, the same post-treatment as in Example 1 was carried out to give a random (isoprene/acrylonitrile) copolymer. The conversion rate of isoprene was 88% and the conversion rate of acrylonitrile was 79%. The analysis results of the random (isoprene/acrylonitrile) polymer obtained are shown in Table 4. The polymer was confirmed to have an iodine atom at the terminal of the polymer chain.

TABLE 4

| | EXAMPLE | | | | | |
|---|---|---|---|---|---|---|
| | 13 | 14 | 15 | 16 | 17 | 18 |
| Raw material Ru complex | (11a) | (11a) | (11a) | (11a) | (11a) | (11a) |
| Amount used (parts) | 1.59 | 1.59 | 1.59 | 1.59 | 1.59 | 1.59 |
| Ligand | AN | AN | AN | AN | AN | AAm |
| Amount used (parts) | 53.0 | 53.0 | 53.0 | 53.0 | 53.0 | 70.1 |
| Solvent for preparation of complex | TOL | TOL | TOL | TOL | TOL | THF |
| Amount used (parts) | 263 | 263 | 263 | 263 | 263 | 269 |
| Ruthenium complex as a polymerization catalyst Activator | Complex (A) | Complex (A) | Complex (A) | Complex (A) | Complex (A) | Complex (D) |
| Amine | TBA | TBA | TBA | TBA | TBA | TBA |
| Amount used (parts) | 3.71 | 37.1 | 3.71 | 3.71 | 3.71 | 3.71 |
| Stabilizer | . . . | . . . | . . . | PPh3 | PPh3 | . . . |
| Amount used (parts) | . . . | . . . | . . . | 1.05 | 1.05 | . . . |
| Internal standard | HX | HX | HX | HX | HX | HX |
| Amount used (parts) | 17.3 | 17.3 | 17.3 | 17.3 | 17.3 | 17.3 |
| Polymerization Monomer | | | | | | |
| Conjugated diene | IP | IP | IP | IP | IP | IP |
| Amount used (parts) | 68.2 | 68.2 | 68.2 | 68.2 | 68.2 | 68.2 |
| Comonomer | AN | AN | AN | AN | AN | AAm |
| Amount used (parts) | (*1) | (*1) | (*1) | (*1) | (*1) | (*1) |
| Organic halide | MBIB | MBIB | EIP | CPN | MBIB | MBIB |
| Amount used (parts) | 3.62 | 3.62 | 4.56 | 1.79 | 3.62 | 3.62 |
| Polymerization solvent | TOL | TOL | TOL | TOL | TOL | THF |
| Amount used (parts) | (*1) | (*1) | (*1) | (*1) | (*1) | (*1) |
| Reaction temperature | 80° C. | 80° C. | 80° C. | 80° C. | 80° C. | 80° C. |
| Reaction time | 137 h | 112 h | 137 h | 90 h | 90 h | 142 h |
| Polymer | Random (IP-AN) copolymer | Random (IP-AN) copolymer | Random (IP-AN) copolymer | Random (IP-AN) copolymer | Random (IP-AN) copolymer | Random (IP-AA) copolymer |
| Conjugated diene conversion rate (%) | 82 | 74 | 88 | 70 | 70 | 55 |
| Comonomer conversion rate (%) | 75 | 71 | 79 | 66 | 69 | 34 |
| Weight-average molecular weight | 8,910 | 3,530 | 6,310 | 3,960 | 6,540 | 1,560 |
| Number-average molecular weight | 4,500 | 2,500 | 3,220 | 2,660 | 3,850 | 1,130 |
| Mw/Mn | 1.98 | 1.41 | 1.96 | 1.49 | 1.70 | 1.38 |
| Ratio (%) of polymer chains having a halogen atom at the terminal | | | | | | |
| Terminal group structure (1) | 4 | 3 | 2 | 3 | 3 | 3 |
| Terminal group structure (2) | 40 | 33 | 23 | 24 | 27 | 28 |
| Terminal group structure (3) | 26 | 56 | 28 | 56 | 33 | 45 |
| TOTAL | 70 | 92 | 53 | 83 | 63 | 76 |

(*1): Added on preparing the catalyst.

Example 16

The ruthenium complex (A) was prepared in the same manner as in Example 10, except that 1.05 parts of triphenylphosphine was further added as a stabilizer, and a polymerization reaction was carried out using the ruthenium complex (A). After 90 hours, the same post-treatment as in Example 1 was carried out to give a random (isoprene/acrylonitrile) copolymer. The conversion rate of isoprene was 70% and the conversion rate of acrylonitrile was 66%. The analysis results of the random (isoprene/acrylonitrile) polymer obtained are shown in Table 4. The polymer was confirmed to have a chlorine atom at the terminal of the polymer chain.

Example 17

The ruthenium complex (A) was prepared in the same manner as in Example 16, except that 3.62 parts of methyl 2-bromoisobutyrate was used as an organic halide in place of 1.79 parts of 2-chloropropionitrile, and a polymerization reaction was carried out using the ruthenium complex (A). The conversion rate of isoprene was 70% and the conversion rate of acrylonitrile was 69%. The analysis results of the random (isoprene/acrylonitrile) polymer obtained are shown in Table 4. The polymer was confirmed to have a bromine atom at the terminal of the polymer chain.

Example 18

Preparation of the Ruthenium Complex (D)

Under nitrogen atmosphere, 1.59 parts of Ru complex (11a), 269 parts of THF as a solvent, 3.71 parts of tributylamine as an activator and 17.3 parts of hexane as an internal standard were introduced into a 30 mL glass reaction vessel, and heated to 80° C. to dissolve Ru complex (11a). Then, was added thereto 70.1 parts of acrylamide as a complex-preparing raw material and monomer, followed by stirring at room temperature for 5 minutes to prepare chloropentamethylcyclopentadienyl triphenylphosphine η²-acrylamide ruthenium (hereinafter, in the Examples, referred to as "the ruthenium complex (D)") in the reaction system.

Polymerization by the Ruthenium Complex (D)

Then, were added thereto 68.2 parts of isoprene and 3.62 parts of methyl 2-bromoisobutyrate as an organic halide, and stirred under heating at 80° C. After 142 hours, the same post-treatment as in Example 1 was carried out to give a random (isoprene/acrylamide) copolymer. The conversion rate of isoprene was 55% and the conversion rate of acrylamide was 34%. The molecular weight in terms of polystyrene of the random (isoprene/acrylamide) copolymer obtained was Mw=1,560, Mn=1,130, and Mw/Mn=1.38. The polymer was confirmed to have 3% of the structure represented by general formula (1), 28% of the structure represented by general formula (2), and 45% of the structure represented by formula (19), which is classified into general formula (3), relative to all polymer chains, respectively, and a bromine atom at one terminal of the polymer chain.

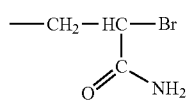

(19)

Example 19

Preparation of the Ruthenium Complex (E)

Under nitrogen atmosphere, 0.54 part of chloropentamethylcyclopentadienyl ruthenium tetramer ([RuCp*(μ₃-Cl)]₄), 263 parts of toluene and 1.22 parts of tri(m-tolyl)phosphine as a ligand were introduced into a 30 mL glass reaction vessel followed by stirring at 80° C. for 1 hour. Then, 2.58 parts of dibutylamine as an activator, 17.3 parts of hexane as an internal standard and 53.0 parts of acrylonitrile as a complex-preparing raw material and monomer were added thereto followed by stirring at room temperature for 5 minutes to prepare chloropentamethylcyclopentadienyl tri(m-tolyl)phosphine η²-acrylonitrile ruthenium (hereinafter, in the Examples, referred to as "the ruthenium complex (E)") in the reaction system.

Polymerization by the Ruthenium Complex (E)

Then, were added thereto 68.2 parts of isoprene and 1.79 parts of 2-chloropropionitrile as an organic halide, and stirred under heating at 80° C. to conduct a polymerization reaction. After 114 hours, the glass reaction vessel was cooled in a dry ice-methanol bath, and the volatiles were distilled off under reduced pressure to give a random (isoprene/acrylonitrile) copolymer. The conversion rate of isoprene was 84% and the conversion rate of acrylonitrile was 76%. The analysis results of the random (isoprene/acrylonitrile) polymer obtained are shown in Table 5. The polymer was confirmed to have a chlorine atom at the terminal of the polymer chain.

Example 20

Preparation of the Ruthenium Complex (F)

Chloropentamethylcyclopentadienyl tri(4-methoxyphenyl)phosphine η²-acrylonitrile ruthenium (hereinafter, in the Examples, referred to as "the ruthenium complex (F)") was prepared in the reaction system in the same manner as in Example 19, except that 1.41 parts of tri(4-methoxyphenyl) phosphine was used as a phosphorus compound of the ligand in place of 1.22 parts of tri(m-tolyl)phosphine.

Polymerization by the Ruthenium Complex (F)

Then, was added thereto 68.2 parts of isoprene and 1.79 parts of 2-chloropropionitrile as an organic halide, followed by stirring at 80° C. to conduct a polymerization reaction. After 114 hours, the same post-treatment as in Example 1 was carried out to give a random (isoprene/acrylonitrile) copolymer. The conversion rate of isoprene was 62% and the conversion rate of acrylonitrile was 64%. The analysis results of the random (isoprene/acrylonitrile) polymer obtained are shown in Table 5. The polymer was confirmed to have a chlorine atom at the terminal of the polymer chain.

TABLE 5

| | EXAMPLE | | | | |
|---|---|---|---|---|---|
| | 19 | 20 | 21 | 22 | 23 |
| Raw material Ru complex | Tetramer | Tetramer | Tetramer | Tetramer | Tetramer |
| Amount used (parts) | 0.54 | 0.54 | 0.54 | 0.54 | 0.54 |
| Ligand | AN | AN | AN | AN | AN |
| Amount used (parts) | 53.0 | 53.0 | 53.0 | 53.0 | 53.0 |
| Phosphine ligand | TTP | TMPP | TTFMPP | TBP | BDPPE |
| Amount used (parts) | 1.22 | 1.41 | 1.87 | 0.81 | 1.59 |
| Solvent for preparation of complex | TOL | TOL | TOL | TOL | TOL |
| Amount used (parts) | 263 | 263 | 263 | 263 | 263 |
| Ruthenium complex as a polymerization catalyst | Complex(E) | Complex(F) | Complex(G) | Complex(H) | Complex(I) |
| Activator | | | | | |
| Amine | DBA | DBA | DBA | DBA | DBA |
| Amount used (parts) | 2.58 | 2.58 | 2.58 | 2.58 | 2.58 |

TABLE 5-continued

| | EXAMPLE | | | | |
|---|---|---|---|---|---|
| | 19 | 20 | 21 | 22 | 23 |
| Internal standard | HX | HX | HX | HX | HX |
| Amount used (parts) | 17.3 | 17.3 | 17.3 | 17.3 | 17.3 |
| Polymerization Monomer | | | | | |
| Conjugated diene | IP | IP | IP | IP | IP |
| Amount used (parts) | 68.2 | 68.2 | 68.2 | 68.2 | 68.2 |
| Comonomer | AN | AN | AN | AN | AN |
| Amount used (parts) | (*1) | (*1) | (*1) | (*1) | (*1) |
| Organic halide | CPN | CPN | CPN | CPN | CPN |
| Amount used (parts) | 1.79 | 1.79 | 1.79 | 1.79 | 1.79 |
| Polymerization solvent | TOL | TOL | TOL | TOL | TOL |
| Amount used (parts) | (*1) | (*1) | (*1) | (*1) | (*1) |
| Reaction temperature | 80° C. | 80° C. | 80° C. | 80° C. | 80° C. |
| Reaction time | 114 h | 114 h | 114 h | 114 h | 114 h |
| Polymer | Random (IP-AN) copolymer | Random (IP-AN) copolymer | Random (IP-AN) copolymer | Random (IP-AN) copolymer | Random (IP-AN) copolymer |
| Conjugated diene conversion rate (%) | 84 | 62 | 70 | 72 | 54 |
| Comonomer conversion rate (%) | 76 | 64 | 67 | 65 | 64 |
| Weight-average molecular weight | 5,370 | 3,780 | 3,310 | 7,200 | 212,600 |
| Number-average molecular weight | 3,190 | 2,440 | 2,550 | 4,060 | 110,300 |
| Mw/Mn | 1.68 | 1.55 | 1.30 | 1.77 | 1.93 |
| Ratio (%) of polymer chains having a halogen atom at the terminal | | | | | |
| Terminal group structure (1) | 3 | 4 | 3 | 3 | |
| Terminal group structure (2) | 25 | 35 | 26 | 40 | 22 |
| Terminal group structure (3) | 64 | 44 | 61 | 40 | 41 |
| TOTAL | 92 | 83 | 90 | 83 | 65 |

*1: Added on preparing the catalyst.

Example 21

Preparation of the Ruthenium Complex (G)

Chloropentamethylcyclopentadienyl tri(p-trifluoromethylphenyl)phosphine $\eta^2$-acrylonitrile ruthenium (hereinafter, in the Examples, referred to as "the ruthenium complex (G)") was prepared in the reaction system in the same manner as in Example 19, except that 1.87 parts of tri(p-trifluoromethylphenyl)phosphine was used as a phosphorus compound as the ligand in place of 1.22 parts of tri(m-tolyl)phosphine.

Polymerization by the Ruthenium Complex (G)

Then, a polymerization reaction was carried out using the ruthenium complex (G) in the same manner as in Example 19. After 114 hours, the same post-treatment as in Example 1 was carried out to give a random (isoprene/acrylonitrile) copolymer. The conversion rate of isoprene was 70% and the conversion rate of acrylonitrile was 67%. The analysis results of the random (isoprene/acrylonitrile) polymer obtained are shown in Table 5. The polymer was confirmed to have a chlorine atom at the terminal of the polymer chain.

Example 22

Preparation of the Ruthenium Complex (H)

Chloropentamethylcyclopentadienyl tri(n-butyl)phosphine $\eta^2$-acrylonitrile ruthenium (hereinafter, in the Examples, referred to as "the ruthenium complex (H)") was prepared in the reaction system in the same manner as in Example 19, except that 0.81 part of tri(n-butyl)phosphine was used as a phosphorus compound as the ligand in place of 1.22 parts of tri(m-tolyl)phosphine.

Polymerization by the Ruthenium Complex (H)

A polymerization reaction was carried out using the ruthenium complex (H) in the same manner as in Example 19. After 114 hours, the same post-treatment as in Example 1 was carried out to give a random (isoprene/acrylonitrile) copolymer. The conversion rate of isoprene was 72% and the conversion rate of acrylonitrile was 65%. The analysis results of the random (isoprene/acrylonitrile) polymer obtained are shown in Table 5. The polymer was confirmed to have a chlorine atom at the terminal of the polymer chain.

Example 23

Preparation of the Ruthenium Complex (I)

Chloropentamethylcyclopentadienyl 1,2-bis(diphenylphosphino)ethane $\eta^2$-acrylonitrile ruthenium (hereinafter, in the Examples, referred to as "the ruthenium complex (I)") was prepared in the reaction system in the same manner as in Example 19, except that 1.59 parts of 1,2-bis(diphenylphosphino)ethane was used as a phosphorus compound as the ligand in place of 1.22 parts of tri(m-tolyl)phosphine Polymerization by the Ruthenium Complex (I)

A polymerization reaction was carried out using the ruthenium complex (I) in the same manner as in Example 19. After 114 hours, the same post-treatment as in Example 1 was carried out to give a random (isoprene/acrylonitrile) copolymer. The conversion rate of isoprene was 54% and the conversion rate of acrylonitrile was 64%. The analysis results of the random (isoprene/acrylonitrile) polymer obtained are shown in Table 5. The polymer was confirmed to have a chlorine atom at the terminal of the polymer chain.

Example 24

Preparation of the Ruthenium Complex (A)

The ruthenium complex (A) was prepared in the same manner as in Example 8, except that the amount of acrylonitrile was changed to 27.1 parts.

Polymerization by the Ruthenium Complex (A)

Then, a polymerization was carried out in the same manner as in Example 8, except that the amount of isoprene was changed to 102.0 parts and that 1.79 parts of 2-chloropropionitrile was used as an organic halide in place of 3.70 parts of methyl α-chlorophenyl acetate. After 142 hours, the same post-treatment as in Example 1 was carried out to give a random (isoprene/acrylonitrile) copolymer. The conversion rate of isoprene was 36% and the conversion rate of acrylonitrile was 90%. The analysis results of the random (isoprene/acrylonitrile) polymer obtained are shown in Table 6. The polymer was confirmed to have a chlorine atom at the terminal of polymer chain.

TABLE 6

|  | EXAMPLE | | | | |
|---|---|---|---|---|---|
|  | 24 | 25 | 26 | 27 | 28 |
| Raw material Ru complex | (11a) | (11a) | (11a) | (11a) | (11a) |
| Amount used (parts) | 1.59 | 1.59 | 1.59 | 1.59 | 1.59 |
| Ligand | AN | AN | AN | AN | AN |
| Amount used (parts) | 27.1 | 79.3 | 53.0 | 53.0 | 53.0 |
| Solvent for preparation of complex | TOL | TOL | TOL | TOL | TOL |
| Amount used (parts) | 263 | 263 | 263 | 263 | 263 |
| Ruthenium complex as a polymerization catalyst | Complex(A) | Complex(A) | Complex(A) | Complex(A) | Complex(A) |
| Activator |  |  |  |  |  |
| Amine | DBA | DBA | TBA | TBA | TBA |
| Amount used (parts) | 2.58 | 2.58 | 3.71 | 3.71 | 3.71 |
| Stabilizer | ... | ... | PPh3 | PPh3 | PPh3 |
| Amount used (parts) | ... | ... | 1.05 | 1.05 | 1.05 |
| Internal standard | HX | HX | HX | HX | HX |
| Amount used (parts) | 17.3 | 17.3 | 17.3 | 17.3 | 17.3 |
| Polymerization Monomer |  |  |  |  |  |
| Conjugated diene | IP | IP | BD | BD | BD |
| Amount used (parts) | 102 | 34.0 | 54.1 | 54.1 | 54.1 |
| Comonomer | AN | AN | AN | AN | AN |
| Amount used (parts) | (*1) | (*1) | (*1) | (*1) | (*1) |
| Organic halide | CPN | CPN | MBIB | MBIB | CPN |
| Amount used (parts) | 1.79 | 1.79 | 3.62 | 0.36 | 1.79 |
| Polymerization solvent | TOL | TOL | TOL | TOL | TOL |
| Amount used (parts) | (*1) | (*1) | (*1) | (*1) | (*1) |
| Reaction temperature | 80° C. | 80° C. | 80° C. | 80° C. | 80° C. |
| Reaction time | 142 h | 142 h | 118 h | 118 h | 118 h |
| Polymer | Random (IP-AN) copolymer | Random (IP-AN) copolymer | Random (BD-AN) copolymer | Random (BD-AN) copolymer | Random (BD-AN) copolymer |
| Conjugated diene conversion rate (%) | 36 | 97 | 50 | 65 | 96 |
| Comonomer conversion rate (%) | 90 | 34 | 64 | 65 | 72 |
| Weight-average molecular weight | 1,970 | 2,100 | 24,370 | 123,200 | 5,550 |
| Number-average molecular weight | 1,290 | 1,330 | 12,310 | 62,490 | 3,410 |
| Mw/Mn | 1.53 | 1.58 | 1.98 | 1.97 | 1.63 |
| Ratio (%) of polymer chains having a halogen atom at the terminal |  |  |  |  |  |
| Terminal group structure (1) | 4 | 1 | 3 | 3 | 3 |
| Terminal group structure (2) | 44 | 17 | 32 | 28 | 26 |
| Terminal group structure (3) | 41 | 69 | 48 | 41 | 57 |
| TOTAL | 89 | 87 | 83 | 72 | 86 |

*1: Added on preparing the catalyst.

Example 25

A preparation of the ruthenium complex (A) and a polymerization reaction using the ruthenium complex (A) were carried out in the same manner as in Example 24, except that the amount of acrylonitrile was changed to 79.3 parts and that the amount of isoprene was changed to 34.0 parts. After 142 hours, the same post-treatment as in Example 1 was carried out to give a random (isoprene/acrylonitrile) copolymer. The conversion rate of isoprene was 97% and the conversion rate of acrylonitrile was 34%. The analysis results of the random (isoprene/acrylonitrile) polymer obtained are shown in Table 6. The polymer was confirmed to have a chlorine atom at the terminal of the polymer chain.

Example 26

Preparation of the Ruthenium Complex (A)

The ruthenium complex (A) was prepared in the same manner as in Example 17, except that 54.1 parts of 1,3-butadiene was used in place of 68.2 parts of isoprene, and a polymerization reaction was carried out using the ruthenium complex (A). After 118 hours, the same post-treatment as in Example 1 was carried out to give a random (butadiene/acrylonitrile) copolymer. The conversion rate of butadiene was 50% and the conversion rate of acrylonitrile was 64%. The molecular weight in terms of polystyrene of the random (butadiene/acrylonitrile) polymer obtained was Mw=24,370, Mn=12,310, and Mw/Mn=1.98. The polymer was confirmed to have 3% of the structure represented by formula (20), which is classified into general formula (1), 32% of the structure general formula represented by formula (21), which is classified into general formula (2), and 48% of the structure represented by general formula (3), relative to all polymer chains, respectively, and a bromine atom at one terminal of the polymer chain.

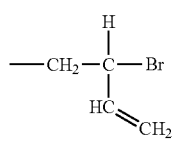
(20)

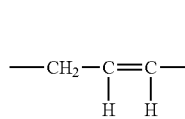
(21)

Example 27

The ruthenium complex (A) was prepared in the same manner as in Example 26, except that the amount of methyl-2-bromoisobutyrate was changed to 0.36 part, and a polymerization reaction was carried out using the ruthenium complex (A) to give a random (butadiene/acrylonitrile) copolymer. The conversion rate of butadiene was 65% and the conversion rate of acrylonitrile was 65%. The molecular weight in terms of polystyrene of the random (butadiene/acrylonitrile) polymer obtained was Mw=123,200, Mn=62,490, and Mw/Mn=1.97. The polymer was confirmed to have 3% of the structure represented by general formula (1), 28% of the structure represented by general formula (2), and 41% of the structure represented by general formula (3), relative to all polymer chains, and a bromine atom at one terminal of the polymer chain.

Example 28

A polymerization reaction was carried out in the same manner as in Example 26, except that 1.79 parts of 2-chloropropionitrile was used as an organic halide in place of 3.62 parts of methyl 2-bromoisobutyrate. After 118 hours, the same post-treatment as in Example 1 was carried out to give a random (butadiene/acrylonitrile) copolymer. The conversion rate of butadiene was 96% and the conversion rate of acrylonitrile was 72%. The molecular weight in terms of polystyrene of the random (butadiene/acrylonitrile) polymer obtained was Mw=5,550, Mn=3,410, and Mw/Mn=1.63. The polymer was confirmed to have 3% of the structure represented by general formula (1), 26% of the structure represented by general formula (2), and 57% of the structure represented by general formula (3), relative to all polymer chains, respectively, and a chlorine atom at one terminal of the polymer chain.

Example 29

The ruthenium complex (A) was prepared in the same manner as in Example 10, except that 345 parts of γ-butyrolactone was used as a solvent in place of 263 parts of toluene, and a polymerization reaction was carried out using the ruthenium complex (A). After 24 hours, the same post-treatment as in Example 1 was carried out to give a random (isoprene/acrylonitrile) copolymer. The conversion rate of isoprene was 71% and the conversion rate of acrylonitrile was 61%. The analysis results of the random (isoprene/acrylonitrile) polymer obtained are shown in Table 7. The polymer was confirmed to have a chlorine atom at the terminal of the polymer chain.

Example 30

The ruthenium complex (A) was prepared in the same manner as in Example 10, except that a mixed solvent of 217 parts of ethylene carbonate with 143 parts of toluene was used as a solvent in place of 263 parts of toluene, and a polymerization reaction was carried out using the ruthenium complex (A). After 24 hours, the same post-treatment as in Example 1 was carried out to give a random (isoprene/acrylonitrile) copolymer. The conversion rate of isoprene was 83% and the conversion rate of acrylonitrile was 70%. The analysis results of the random (isoprene/acrylonitrile) copolymer obtained are shown in Table 7. The polymer was confirmed to have a chlorine atom at the terminal of the polymer chain.

Example 31

The ruthenium complex (A) was prepared in the same manner as in Example 10, except that 373 parts of propylene carbonate was used as a solvent in place of 263 parts of toluene, and a polymerization reaction was carried out using the ruthenium complex (A). After 24 hours, the same post-treatment as in Example 1 was carried out to give a random (isoprene/acrylonitrile) copolymer. The conversion rate of isoprene was 81% and the conversion rate of acrylonitrile was 66%. The analysis results of the random (isoprene/acrylonitrile) copolymer obtained are shown in Table 7. The polymer was confirmed to have a chlorine atom at the terminal of the polymer chain.

TABLE 7

| | EXAMPLE | | | |
|---|---|---|---|---|
| | 29 | 30 | 31 | 32 |
| Raw material Ru complex | (11a) | (11a) | (11a) | (11a) |
| Amount used (parts) | 1.59 | 1.59 | 1.59 | 1.59 |
| Ligand | AN | AN | AN | AN |
| Amount used (parts) | 53.0 | 53.0 | 53.0 | 53.0 |
| Solvent for preparation of complex | γBL | TOL/EC | PC | TOL |
| Amount used (parts) | 345 | 143/217 | 373 | 262 |
| Ruthenium complex as a polymerization catalyst | Complex(A) | Complex(A) | Complex(A) | Complex(A) |
| Activator | | | | |
| Amine | TBA | TBA | TBA | TBA |
| Amount used (parts) | 3.71 | 3.71 | 3.71 | 3.71 |
| Internal standard | HX | HX | HX | HX |
| Amount used (parts) | 17.3 | 17.3 | 17.3 | 17.3 |
| Polymerization | | | | |
| Monomer | | | | |
| Conjugated diene | IP | IP | IP | IP |
| Amount used (parts) | 68.2 | 68.2 | 68.2 | 68.2 |
| Comonomer | AN | AN | AN | AN |
| Amount used (parts) | (*1) | (*1) | (*1) | (*1) |
| Organic halide | CPN | CPN | CPN | MCPA |
| Amount used (parts) | 1.79 | 1.79 | 1.79 | 3.70 |
| Radical generator | ... | ... | ... | AIBN |
| Amount used (parts) | ... | ... | ... | 8.25 |
| Polymerization solvent | γBL | TOL/EC | PC | TOL |
| Amount used (parts) | (*1) | (*1) | (*1) | (*1) |
| Reaction temperature | 80° C. | 80° C. | 80° C. | 80° C. |
| Reaction time | 24 h | 24 h | 24 h | 72 h |
| Polymer | Random (IP-AN) copolymer | Random (IP-AN) copolymer | Random (IP-AN) copolymer | Random (IP-AN) copolymer |
| Conjugated diene conversion rate (%) | 71 | 83 | 81 | 78 |
| Comonomer conversion rate (%) | 61 | 70 | 66 | 68 |
| Weight-average molecular weight | 9,470 | 11,970 | 12,170 | 10,000 |
| Number-average molecular weight | 5,450 | 7,140 | 7,050 | 6,900 |
| Mw/Mn | 1.74 | 1.68 | 1.73 | 1.45 |
| Ratio (%) of polymer chains having a halogen atom at the terminal | | | | |
| Terminal group structure (1) | 2 | 2 | 2 | 2 |
| Terminal group structure (2) | 21 | 22 | 22 | 21 |
| Terminal group structure (3) | 60 | 51 | 51 | 35 |
| TOTAL | 83 | 75 | 75 | 58 |

Example 32

A random (isoprene/acrylonitrile) copolymer was prepared in the same manner as in Example 10, except that the amount of toluene was changed to 262 parts, that 3.70 parts of methyl α-chlorophenyl acetate was used as an organic halide in place of 1.79 parts of 2-chloropropionitrile, that 8.25 parts of 2,2'-azobis(isobutyronitrile) (hereinafter, sometimes referred to as "AIBN") was further added as a radical generator, and that the reaction time was changed to 72 hours. The conversion rate of isoprene was 78% and the conversion rate of acrylonitrile was 68%. The analysis results of the random (isoprene/acrylonitrile) copolymer obtained are shown in Table 7. The polymer was confirmed to have a chlorine atom at one terminal of the polymer chain.

Example 33

Preparation of the Ruthenium Complex (J)

Under nitrogen atmosphere, 1.69 parts of ruthenium complex (11b) obtained in Synthesis Example 4, 262 parts of toluene as a solvent, 3.71 parts of tributylamine as an activator and 17.3 parts of hexane as an internal standard were introduced into a 30 mL glass reaction vessel, and heated to 80° C. to dissolve ruthenium complex (11b). Then, was added thereto 53.0 parts of acrylonitrile as a complex-preparing raw material and monomer, followed by stirring at room temperature for 5 minutes to generate bromopentamethylcyclopentadienyl triphenylphosphine η²-acrylonitrile ruthenium (hereinafter, referred to as "the ruthenium complex (J)") in the reaction system.

Polymerization by the Ruthenium Complex (J)

Then, were added thereto 68.2 parts of isoprene as a monomer and 3.9 parts of ethyl α-bromoisobutyrate as an organic halide, and stirred under heating at 80° C. After 120 hours, the same post-treatment as in Example 1 was carried out to give a random (isoprene/acrylonitrile) copolymer. The conversion rate of isoprene was 74% and the conversion rate of acrylonitrile was 70%. The molecular weight in terms of polystyrene of the random (isoprene/acrylonitrile) copolymer obtained was Mw=9,300, Mn=6,200, and Mw/Mn=1.50. The random (isoprene/acrylonitrile) copolymer obtained was confirmed to have 3% of the structure represented by general formula (1), 32% of the structure represented by general formula (2) and 50% of the structure represented by general formula (3), relative to the total polymer chains, respectively, and a bromine atom at one terminal of the polymer chain.

Example 34

Preparation of the Ruthenium Complex (J)

Under nitrogen atmosphere, 1.69 parts of ruthenium complex (11b), 262 parts of toluene as a solvent, 3.71 parts of tributylamine as an activator and 17.3 parts of hexane as an internal standard were introduced into a 30 mL glass reaction vessel, and heated to 80° C. to dissolve ruthenium complex (11b). Then, 8.25 parts of 2,2'-azobis(isobutyronitrile) as a radical generator and 53.0 parts of acrylonitrile as a complex-preparing raw material and monomer were added thereto, followed by stirring at room temperature for 5 minutes to prepare the ruthenium complex (J) in the reaction system.

Polymerization by the Ruthenium Complex (J)

Then, were added thereto 68.2 parts of isoprene as a monomer, 3.9 parts of ethyl α-bromoisobutyrate as an organic halide and 17.3 parts of hexane as an internal standard, and stirred under heating at 80° C. After 72 hours, the same post-treatment as in Example 1 was carried out to give a random (isoprene/acrylonitrile) copolymer. The conversion rate of isoprene was 76% and the conversion rate of acrylonitrile was 67%. The molecular weight in terms of polystyrene of the random (isoprene/acrylonitrile) copolymer obtained was Mw=10,400, Mn=7,300, and Mw/Mn=1.43. The polymer was confirmed to have 2% of the structure represented by general formula (1), 24% of the structure represented by general formula (2), and 40% of the structure represented by general formula (3), relative to the total polymer chains, respectively, (provided that all X's are Br in formulae (1) to (3)), and a bromine atom at one terminal of the polymer chain.

Example 35

Preparation of Ruthenium Complex (J)

The ruthenium complex (J) was prepared in the same manner as in Example 33, except that the heating temperature was changed from 80° C. to 60° C.

Polymerization by Ruthenium Complex (J)

Then, were added thereto 68.2 parts of isoprene as a monomer and 3.9 parts of ethyl α-bromoisobutyrate as an organic halide and stirred under heating at 60° C. After 72 hours, the same post-treatment as in Example 1 was carried out to give a random (isoprene/acrylonitrile) copolymer. The conversion rate of isoprene was 28% and the conversion rate of acrylonitrile was 22%. The molecular weight in terms of polystyrene of the random (isoprene/acrylonitrile) copolymer obtained was Mw=4,400, Mn=2,900, and Mw/Mn=1.52. The random (isoprene/acrylonitrile) copolymer obtained was confirmed to have 4% of the structure represented by general formula (1), 39% of the structure represented by general formula (2), and 50% of the structure represented by general formula (3), relative to all polymer chains, respectively, and a bromine atom at one terminal of the polymer chain.

Example 36

A random (isoprene/acrylonitrile) copolymer was obtained in the same manner as in Example 34, except that the stirring temperature under heating was changed to 60° C. The conversion rate of isoprene was 63% and the conversion rate of acrylonitrile was 55%. The analysis results of the random (isoprene/acrylonitrile) copolymer obtained are shown in Table 8. The polymer was confirmed to have a bromine atom at one terminal of the polymer chain. The numerical value of polydispersity shows that the molecular weight distribution can be controlled, even when AIBN is added.

Example 37

A random (isoprene/acrylonitrile) copolymer was obtained in the same manner as in Example 36, except that the amount of AIBN was changed from 8.25 parts to 33.0 parts. The conversion rate of isoprene was 94% and the conversion rate of acrylonitrile was 78%. The analysis results of the random (isoprene/acrylonitrile) copolymer obtained are shown in Table 8. The polymer was confirmed to have a bromine atom at one terminal of the polymer chain.

This Example shows that high polymerization activation can be achieved by an increased amount of AIBN while controlling the polydispersity.

Example 38

A random (isoprene/acrylonitrile) copolymer was obtained in the same manner as in Example 32, except that 11.5 parts of dimethyl 2,2'-azobis(isobutyrate) was used in place of 8.25 parts of AIBN. The conversion rate of isoprene was 67% and the conversion rate of acrylonitrile was 57%. The analysis results of the random (isoprene/acrylonitrile) copolymer obtained are shown in Table 8. The polymer was confirmed to have a bromine atom at one terminal of the polymer chain.

This Example shows that the same effects can be achieved, even when a non-azo initiator is used in place of the azo initiator.

Comparative Example 1

Under nitrogen atmosphere, 263 parts of toluene, 53.0 parts of acrylonitrile and 68.2 parts of isoprene were introduced into a 30 mL glass reaction vessel, and 0.33 part of azobisisobutyronitrile was further added thereto, and stirred under heating at 80° C. After reaction for 15 hours, the same post-treatment as in Example 1 was carried out to give a random (isoprene/acrylonitrile) copolymer. The conversion rate of isoprene was 72% and the conversion rate of acrylonitrile was 60%. The molecular weight in terms of the polystyrene of the random (isoprene/acrylonitrile) polymer obtained was Mw=35,200, Mn=12,300 and Mw/Mn=2.86. The results of $^1$H-NMR analysis of the random (isoprene/acrylonitrile) copolymer obtained show that the polymer has no halogen at a terminal of the polymer chain.

TABLE 8

| | EXAMPLE | | | | | |
|---|---|---|---|---|---|---|
| | 33 | 34 | 35 | 36 | 37 | 38 |
| Raw material Ru complex | (11b) | (11b) | (11b) | (11b) | (11b) | (11a) |
| Amount used (parts) | 1.69 | 1.69 | 1.69 | 1.69 | 1.69 | 1.69 |
| Ligand | AN | AN | AN | AN | AN | AN |
| Amount used (parts) | 53.0 | 53.0 | 53.0 | 53.0 | 53.0 | 53.0 |
| Solvent for preparation of complex | TOL | TOL | TOL | TOL | TOL | TOL |
| Amount used (parts) | 262 | 262 | 262 | 262 | 262 | 262 |
| Ruthenium complex as a polymerization catalyst | Complex (J) | Complex (J) | Complex (J) | Complex (J) | Complex (J) | Complex (A) |
| Activator | | | | | | |
| Amine | TBA | TBA | TBA | TBA | TBA | TBA |
| Amount used (parts) | 3.71 | 3.71 | 3.71 | 3.71 | 3.71 | 3.71 |
| Internal standard | HX | HX | HX | HX | HX | HX |
| Amount used (parts) | 17.3 | 17.3 | 17.3 | 17.3 | 17.3 | 17.3 |
| Polymerization | | | | | | |
| Monomer | | | | | | |
| Conjugated diene | IP | IP | IP | IP | IP | IP |
| Amount used (parts) | 68.2 | 68.2 | 68.2 | 68.2 | 68.2 | 68.2 |
| Comonomer | AN | AN | AN | AN | AN | AN |
| Amount used (parts) | (*1) | (*1) | (*1) | (*1) | (*1) | (*1) |
| Organic halide | EBIB | EBIB | EBIB | EBIB | EBIB | EBIB |
| Amount used (parts) | 3.9 | 3.9 | 3.9 | 3.9 | 3.9 | 3.9 |
| Radical generator | . . . | AIBN | . . . | AIBN | AIBN | DMABIB |
| Amount used (parts) | . . . | 8.25 | . . . | 8.25 | 33.0 | 11.5 |
| Polymerization solvent | TOL | TOL | TOL | TOL | TOL | TOL |
| Amount used (parts) | (*1) | (*1) | (*1) | (*1) | (*1) | (*1) |
| Reaction temperature | 80° C. | 80° C. | 60° C. | 60° C. | 60° C. | 60° C. |
| Reaction time | 120 h | 72 h | 72 h | 72 h | 72 h | 72 h |
| Polymer | Random (IP-AN) copolymer | Random (IP-AN) copolymer | Random (IP-AN) copolymer | Random (IP-AN) copolymer | Random (IP-AN) copolymer | Random (IP-AN) copolymer |
| Conjugated diene conversion rate (%) | 74 | 76 | 28 | 63 | 94 | 67 |
| Comonomer conversion rate (%) | 70 | 67 | 22 | 55 | 78 | 57 |
| Weight-average molecular weight | 9,300 | 10,400 | 4,400 | 12,200 | 13,100 | 13,200 |
| Number-average molecular weight | 6,200 | 7,300 | 2,900 | 8,100 | 8,600 | 8,700 |
| Mw/Mn | 1.50 | 1.42 | 1.52 | 1.51 | 1.52 | 1.52 |
| Ratio (%) of polymer chains having a halogen atom at the terminal | | | | | | |
| Terminal group structure (1) | 3 | 2 | 4 | 2 | 1 | 2 |
| Terminal group structure (2) | 32 | 17 | 39 | 21 | 10 | 19 |
| Terminal group structure (3) | 50 | 30 | 50 | 33 | 12 | 21 |
| TOTAL | 85 | 49 | 93 | 56 | 23 | 42 |

(*1): Added on preparing the catalyst.

Comparative Example 2

Under nitrogen atmosphere, 2.87 parts of copper bromide, 263 parts of toluene, 5.81 parts of N,N,N',N'',N''-pentamethyldiethylenetriamine, 53.0 parts of acrylonitrile, 68.2 parts of isoprene and 3.70 parts of methyl α-chlorophenyl acetate were introduced into a 30 mL glass reaction vessel, followed by stirring at 80° C. After the reaction for 24 hours, the same post-treatment as in Example 1 was carried out to give a polymer. The conversion rate of isoprene was 21% and the conversion rate of acrylonitrile was 27%. The molecular weight in terms of the polymer obtained was Mw=370, Mn=360 and Mw/Mn=1.04, in other words, the polymer obtained is an oligomer.

[Vulcanization Test]

There were incorporated 100 parts of GPF Carbon Black ("SEAST V", manufactured by Tokai Carbon Co., Ltd.), 5 parts of zinc oxide ("Zinc Oxide No. 1", manufactured by Seido Chemical Industry Co., Ltd.), 1 part of stearic acid, 2 parts of 2,2,4-trimethyl-1,2-dihydroquinoline polymer ("NOCRAC 224", manufactured by Ouchi Shinko Chemical Industrial Co., Ltd.), 8 parts of dioctyl adipate, 1 part of 325 mesh sulfur, 1 part of cyclohexylbenzothiazolylsulfenamide ("NOCCELER-CZ", manufactured by Ouchi Shinko Chemical Industrial Co., Ltd.), 1 part of tetramethylthiuram disulfide ("NOCCELER-TT", manufactured by Ouchi Shinko Chemical Industrial Co., Ltd.), and 1 part of N-(cyclohexylthio)phthalimide ("Santoguard PVI", manufactured by Mitsubishi Monsanto Chemical Co.) into 100 parts of each of the polymers obtained in Examples 1 to 38 and Comparative Examples 1 and 2 to give vulcanizable compositions. Each of the vulcanizable compositions obtained was press vulcanized under a condition of 148° C.×30 minutes for preparing a vulcanized test piece. Vulcanized test pieces were obtained with its shape retained, except for the case where the polymer obtained in Comparative Example 2 was used. In the case where the polymer obtained in Comparative Example 2 was used, the shape of the test piece was not retained.

Explanation for abbreviations used in the Tables.

Phosphine Ligand:
 TTP tri(m-tolyl)phosphine
 TMPP tri(4-methoxyphenyl)phosphine
 TTFMPP tri(p-trifluoromethylphenyl)phosphine
 TBP tri(n-butyl)phosphine
 BDPPE 1,2-bis(diphenylphosphino)ethane Solvent:
 TOL toluene
 γBL γ-butyrolactone
 PC propylene carbonate
 EC ethylene carbonate
 THF tetrahydrofuran Amine:
 DBA dibutylamine
 TBA tributylamine Metal Alkoxide:
 TTIP titanium tetraisopropoxide Stabilizer:
 PPh3 triphenylphosphine Internal Standard:
 HX hexane Monomer:
 IP isoprene
 AN acrylonitrile
 BD butadiene
 MA methyl acrylate
 MMA methyl methacrylate
 ST styrene
 AAm acrylamide Initiator:
 AIBN 2,2'-azobisisobutyronitrile
 DMABIB dimethyl azobisisobutyrate Organic Halide:
 MCPA methyl α-chlorophenyl acetate
 CPN 2-chloropropionitrile
 MBIB methyl 2-bromoisobutyrate
 EBIB ethyl α-bromoisobutyrate
 EIP ethyl 2iodopropionate

The invention claimed is:

1. A method for producing a conjugated diene polymer, which comprises subjecting a monomer containing at least a conjugated diene to living radical polymerization using a polymerization initiator comprising a halogenocyclopentadienyl triorganophosphine η²-olefin ruthenium complex represented by formula (6) and an organic halide

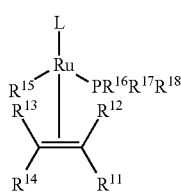

(6)

wherein in formula (6) $R^{11}$, $R^{12}$, $R^{13}$ and $R^{14}$ each represent a hydrogen atom, a cyano group, a carbonyl group represented by formula (7), an ester group represented by formula (8), an amide group represented by formula (9), a nitro group, or a halogen atom with the proviso that at least one of $R^{11}$, $R^{12}$, $R^{13}$ and $R^{14}$ is not a hydrogen atom; $R^{15}$ represents a chlorine atom, a bromine atom or an iodine atom; $R^{16}$, $R^{17}$ and $R^{18}$ each represent an optionally substituted organic group having 1 to 10 carbon atoms; $R^{16}$, $R^{17}$ and $R^{18}$ are the same as or different from each other; and L represents an optionally substituted cyclopentadienyl ring,

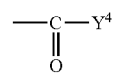

(7)

wherein in formula (7) $Y^4$ represents a hydrogen atom or an optionally substituted hydrocarbon group having 1 to 10 carbon atoms,

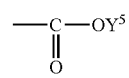

(8)

wherein in formula (8) $Y^5$ represents a hydrogen atom or an optionally substituted organic group having 1 to 10 carbon atoms, and

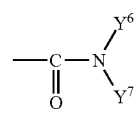

(9)

wherein in formula (9) $Y^6$ and $Y^7$ each represent a hydrogen atom or an optionally substituted hydrocarbon group having 1 to 10 carbon atoms, wherein the conjugated diene polymer comprises at least a conjugated diene monomer unit, wherein the conjugated diene polymer has a number-average molecular weight (Mn) in terms of polystyrene of 1,000 to 1,000,000, a ratio (Mw/Mn) of a weight-average molecular weight (Mw) to the number-average molecular weight (Mn) of lower than 2.0 and the conjugated diene polymer bears a halogen atom at a terminal of the polymer chain, and wherein 10% or higher of all conjugated diene polymer chains have a halogen atom at its terminal.

2. The method of claim 1, wherein the conjugated diene polymer has at least one group selected from the group consisting of a group represented by formula (1), a group represented by formula (2), and a group represented by formula (3), as a terminal group of the polymer chain,

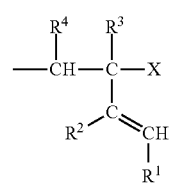

(1)

wherein in formula (1) X represents a chlorine atom, a bromine atom or an iodine atom; and $R^1$, $R^2$, $R^3$ and $R^4$ each represent a hydrogen atom, an optionally substituted hydrocarbon group having 1 to 10 carbon atoms, or a halogen atom,

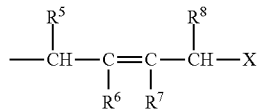

(2)

wherein in formula (2) X represents a chlorine atom, a bromine atom or an iodine atom; and $R^5$, $R^6$, $R^7$ and $R^8$ each represent a hydrogen atom, an optionally substituted hydrocarbon group having 1 to 10 carbon atoms, or a halogen atom,

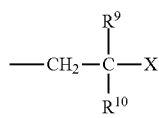

(3)

wherein in formula (3) X represents a chlorine atom, a bromine atom or an iodine atom; $R^9$ represents an aryl group, a cyano group, an ester group represented by formula (4), an amide group represented by formula (5), or a halogen atom; and $R^{10}$ represents a hydrogen atom or a methyl group,

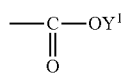

(4)

wherein in formula (4) $Y^1$ represents a hydrogen atom or an optionally substituted organic group having 1 to 10 carbon atoms, and

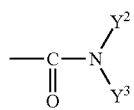

(5)

wherein in formula (5) $Y^2$ and $Y^3$ each represent a hydrogen atom or an optionally substituted organic group having 1 to 10 carbon atoms; and $Y^2$ and $Y^3$ may be the same as or different from each other.

3. The method of claim 1, wherein a ligand represented by formula (10) in the complex of formula (6) is an electron-withdrawing olefin copolymerizable with the conjugated diene monomer,

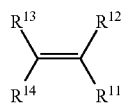

(10)

wherein in formula (10) $R^{11}$, $R^{12}$, $R^{13}$ and $R^{14}$ are the same as $R^{11}$, $R^{12}$, $R^{13}$ and $R^{14}$, respectively, of formula (6).

4. The method of claim 2, wherein a ligand represented by formula (10) in the complex of formula (6) is an electron-withdrawing olefin copolymerizable with the conjugated diene monomer,

(10)

wherein in formula (10) $R^{11}$, $R^{12}$, $R^{13}$ and $R^{14}$ are the same as $R^{11}$, $R^{R12}$, $R^{13}$ and $R^{14}$, respectively, of formula (6).

5. The method of claim 1, wherein the polymerization is carried out by causing a halogenocyclopentadienyl bis(triorganophosphine) ruthenium represented by formula (11) to react with an electron-withdrawing olefin in a polymerization solvent to form a halogenocyclopentadienyl triorganophosphine η²-olefin ruthenium complex represented by formula (6) in the reaction system, and then adding a monomer, containing at least a conjugated diene monomer, and an organic halide to the complex,

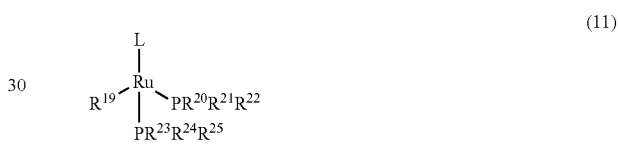

(11)

wherein in formula (11) L is the same as L of formula (6); $R^{19}$ is the same as $R^{15}$ of formula (6); $R^{20}$ to $R^{25}$ each represent an optionally substituted organic group having 1 to 10 carbon atoms and may be the same as or different from each other; and either $R^{20}$ to $R^{22}$ or $R^{23}$ to $R^{25}$ corresponds to $R^{16}$ to $R^{18}$ of formula (6).

6. The method of claim 2, wherein the polymerization is carried out by causing a halogenocyclopentadienyl bis(triorganophosphine) ruthenium represented by formula (11) to react with an electron-withdrawing olefin in a polymerization solvent to form a halogenocyclopentadienyl triorganophosphine η²-olefin ruthenium complex represented by formula (6) in the reaction system, and then adding a monomer, containing at least a conjugated diene monomer, and an organic halide to the complex,

(11)

wherein in formula (11) L is the same as L of formula (6); $R^{19}$ is the same as $R^{15}$ of formula (6); $R^{20}$ to $R^{25}$ each represent an optionally substituted organic group having 1 to 10 carbon atoms and may be the same as or different from each other; and either $R^{20}$ to $R^{22}$ or $R^{23}$ to $R^{25}$ corresponds to $R^{16}$ to $R^{18}$ of formula (6).

7. The method of claim 3, wherein the polymerization is carried out by causing a halogenocyclopentadienyl bis(triorganophosphine) ruthenium represented by formula (11) to react with an electron-withdrawing olefin in a polymerization solvent to form a halogenocyclopentadienyl triorganophosphine $\eta^2$-olefin ruthenium complex represented by formula (6) in the reaction system, and then adding a monomer, containing at least a conjugated diene monomer, and an organic halide to the complex,

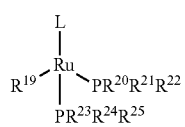

(11)

wherein in formula (11) L is the same as L of formula (6); $R^{19}$ is the same as $R^{15}$ of formula (6); $R^{20}$ to $R^{25}$ each represent an optionally substituted organic group having 1 to 10 carbon atoms and may be the same as or different from each other; and either $R^{20}$ to $R^{22}$ or $R^{23}$ to $R^{25}$ corresponds to $R^{16}$ to $R^{18}$ of formula (6).

8. The method of claim 1, wherein the polymerization is carried out by causing a halogenocyclopentadienyl ruthenium tetramer represented by formula (12), a phosphine compound represented by $PR^{16}R^{17}R^{18}$ in which $R^{16}$, $R^{17}$ and $R^{18}$ are the same as $R^{16}$, $R^{17}$ and $R^{18}$ of formula (6) and an electron-withdrawing olefin represented by formula (10) to react in a polymerization solvent to form a halogenocyclopentadienyl triorganophosphine $\eta^2$-olefin ruthenium complex represented by formula (6) in the reaction system, and then adding a monomer, containing at least a conjugated diene monomer, and an organic halide to the complex, $$[LRu(\mu_3-X)]_4 \quad (12)$$

wherein in formula (12) L is the same as L of formula (6); and X represents a chlorine atom, a bromine atom or an iodine atom.

9. The method of claim 2, wherein the polymerization is carried out by causing a halogenocyclopentadienyl ruthenium tetramer represented by formula (12), a phosphine compound represented by PR $^{16}R^{17}R^{18}$ b in which $R^{16}$, $R^{17}$ and $R^{18}$ are the same as $R^{16}$, $R^{17}$ and $R^{18}$ of formula (6) and an electron-withdrawing olefin represented by formula (10) to react in a polymerization solvent to form a halogenocyclopentadienyl triorganophosphine $\eta^2$-olefin ruthenium complex represented by formula (6) in the reaction system, and then adding a monomer, containing at least a conjugated diene monomer, and an organic halide to the complex $$[LRu(\mu_3-X)]_4 \quad (12)$$

wherein in formula (12) L is the same as L of formula (6); and X represents a chlorine atom, a bromine atom or an iodine atom.

10. The method of claim 3, wherein the polymerization is carried out by causing a halogenocyclopentadienyl ruthenium tetramer represented by formula (12), a phosphine compound represented by $PR^{16}R^{17}R^{18}$ in which $R^{16}$, $R^{17}$ and $R^{18}$ are the same as $R^{16}$, $R^{17}$ and $R^{18}$ of formula (6) and an electron-withdrawing olefin represented by formula (10) to react in a polymerization solvent to form a halogenocyclopentadienyl triorganophosphine $\eta^2$-olefin ruthenium complex represented by formula (6) in the reaction system, and then adding a monomer, containing at least a conjugated diene monomer, and an organic halide to the complex $$[LRu(\mu_3-X)]_4 \quad (12)$$

wherein in formula (12) L is the same as L of formula (6); and X represents a chlorine atom, a bromine atom or an iodine atom.

11. The method of claim 1, wherein the monomer containing at least a conjugated diene monomer is subjected to living radical polymerization using the polymerization initiator comprising the halogenocyclopentadienyl triorganophosphine $\eta^2$-olefin ruthenium complex represented by formula (6) and the organic halide in combination with an organic amine or a metal alkoxide as an activator.

12. The method of claim 2, wherein the monomer containing at least a conjugated diene monomer is subjected to living radical polymerization using the polymerization initiator comprising the halogenocyclopentadienyl triorganophosphine $\eta^2$-olefin ruthenium complex represented by formula (6) and the organic halide in combination with an organic amine or a metal alkoxide as an activator.

13. The method of claim 3, wherein the monomer containing at least a conjugated diene monomer is subjected to living radical polymerization using the polymerization initiator comprising the halogenocyclopentadienyl triorganophosphine $\eta^2$-olefin ruthenium complex represented by formula (6) and the organic halide in combination with an organic amine or a metal alkoxide as an activator.

14. The method of claim 1, wherein the polymerization is carried out by adding the monomer containing at least a conjugated diene monomer, and the organic halide to the halogenocyclopentadienyl triorganophosphine $\eta^2$-olefin ruthenium complex represented by formula (6) in a polymerization solvent.

15. The method of claim 2, wherein the polymerization is carried out by adding the monomer, containing at least a conjugated diene monomer, and the organic halide to the halogenocyclopentadienyl triorganophosphine $\eta^2$-olefin ruthenium complex represented by formula (6) in a polymerization solvent.

16. The method of claim 3, wherein the polymerization is carried out by adding the monomer, containing at least a conjugated diene monomer, and the organic halide to the halogenocyclopentadienyl triorganophosphine $\eta^2$-olefin ruthenium complex represented by formula (6) in a polymerization solvent.

17. The method of claim 1, wherein a radical initiator is further used in combination,
    wherein the radical initiator is selected from an azo compound, an organic peroxide and a nonpolar radical initiator.

18. The method of claim 1, wherein a phosphine as a stabilizer is added to the polymerization reaction system.

19. The method of claim 1, wherein a cyclic ester or a cyclic carbonate is used as a polymerization solvent.

20. A ruthenium complex represented by formula (6),

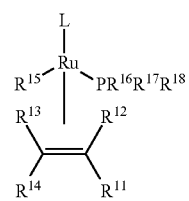

(6)

wherein in formula (6), $R^{11}$, $R^{12}$, $R^{13}$ and $R^{14}$ each represent a hydrogen atom, a cyano group, a carbonyl group represented by formula (7), an ester group represented by formula (8), an amide group represented by formula (9), a nitro group, or a halogen atom, $R^{15}$ represents a chlorine atom, a bromine atom or an iodine atom; $R^{16}$, $R^{17}$ and $R^{18}$ each represent an optionally substituted organic group having 1 to 10 carbon atoms; $R^{16}$, $R^{17}$ and $R^{18}$ are the same as or different from each other; and L represents an optionally substituted cyclopentadienyl ring; and at least two of $R^{11}$, $R^{12}$, $R^{13}$ and $R^{14}$ are not a hydrogen atom,

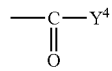

(7)

wherein in formula (7) $Y^4$ represents a hydrogen atom or an optionally sustituted hydrocarbon group having 1 to 10 carbon atoms,

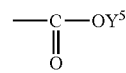

(8)

wherein in formula (8) $Y^5$ represents a hydrogen atom or an optionally substituted organic group having 1 to 10 carbon atoms, and

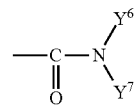

(9)

wherein in formula (9) $Y^6$ and $Y^7$ each represent a hydrogen atom or an optionally substituted hydrocarbon group 1 to 10 carbon atoms.

\* \* \* \* \*